(12) United States Patent
Georgeson et al.

(10) Patent No.: US 9,834,323 B2
(45) Date of Patent: Dec. 5, 2017

(54) AUTOMATED SCANNING SYSTEMS FOR NON-DESTRUCTIVE INSPECTION OF CURVED CYLINDER-LIKE WORKPIECES

(71) Applicant: The Boeing Company, Chicago, IL (US)

(72) Inventors: Gary E. Georgeson, Tacoma, WA (US); Barry A. Fetzer, Renton, WA (US); James J. Troy, Issaquah, WA (US); Scott W. Lea, Renton, WA (US)

(73) Assignee: The Boeing Company, Chicago, IL (US)

( * ) Notice: Subject to any disclaimer, the term of this patent is extended or adjusted under 35 U.S.C. 154(b) by 648 days.

(21) Appl. No.: 14/279,355

(22) Filed: May 16, 2014

(65) Prior Publication Data
US 2015/0329221 A1   Nov. 19, 2015

(51) Int. Cl.
*B64F 5/00* (2017.01)
*G01N 29/265* (2006.01)
(Continued)

(52) U.S. Cl.
CPC ....... *B64F 5/0045* (2013.01); *G01N 29/0654* (2013.01); *G01N 29/265* (2013.01);
(Continued)

(58) Field of Classification Search
CPC .............. G01N 29/265; G01N 29/041; G01N 2291/2634; B64F 5/0045
See application file for complete search history.

(56) References Cited

U.S. PATENT DOCUMENTS 2,344,015 A  3/1944 Allred
3,921,440 A  11/1975 Toth
(Continued)

FOREIGN PATENT DOCUMENTS

FR    2344015 A1   10/1977

OTHER PUBLICATIONS

Extended European Search Report, European Patent Application No. 15165215.3 (European counterpart to the instant patent application).
(Continued)

*Primary Examiner* — Leslie J Evanisko
(74) *Attorney, Agent, or Firm* — Ostrager Chong Flaherty & Broitman P.C.

(57) ABSTRACT

Systems and methods for high-speed non-destructive inspection of a half- or full-barrel-shaped workpiece, such as a barrel-shaped section of an aircraft fuselage. Such workpieces can be scanned externally using a mobile (e.g., translating) arch gantry system comprising a translatable arch frame disposed outside the fuselage section, a carriage that can travel along a curved track carried by the arch frame, a radially inward-extending telescopic arm having a proximal end fixedly coupled to the carriage, and an NDI sensor unit coupled to a distal end of the telescoping arm. The stiffeners of the fuselage sections can be scanned using a mobile scanner platform disposed inside the fuselage section, which platform comprises a radially outward-extending telescopic arm rotatably coupled to a mobile (e.g., holonomic or linear motion) platform and an NDI sensor unit coupled to a distal end of the telescoping arm. The scan data is matched with position data acquired using any one of a plurality of tracking systems to enable the display of NDI features/flaws on a three-dimensional representation of the workpiece.

23 Claims, 17 Drawing Sheets

(51) Int. Cl.
*G01N 29/06* (2006.01)
*G01N 29/44* (2006.01)

(52) U.S. Cl.
CPC ..... *G01N 29/44* (2013.01); *G01N 2291/0231* (2013.01); *G01N 2291/0258* (2013.01); *G01N 2291/0289* (2013.01); *G01N 2291/2634* (2013.01); *G01N 2291/2694* (2013.01)

(56) References Cited

U.S. PATENT DOCUMENTS

| | | | |
|---|---|---|---|
| 5,992,236 A * | 11/1999 | White | G01N 29/043 73/622 |
| 6,137,853 A | 10/2000 | Duckering et al. | |
| 6,247,367 B1 * | 6/2001 | Bar-Cohen | G01N 29/041 73/620 |
| 7,249,512 B2 | 7/2007 | Kennedy et al. | |
| 7,643,893 B2 | 1/2010 | Troy et al. | |
| 7,743,660 B2 | 6/2010 | Marsh et al. | |
| 7,859,655 B2 | 12/2010 | Troy et al. | |
| 2008/0125896 A1 | 5/2008 | Troy et al. | |
| 2010/0275694 A1 | 11/2010 | Roberts | |
| 2011/0137615 A1 | 6/2011 | Motzer et al. | |
| 2011/0178727 A1 | 7/2011 | Hafenrichter et al. | |
| 2013/0145850 A1 | 6/2013 | Lute, Jr. et al. | |
| 2014/0345384 A1 * | 11/2014 | Nguyen | G01N 29/265 73/602 |

OTHER PUBLICATIONS

Partial European Search Report, European Application No. 15165215.3 (European counterpart of the instant patent application), dated Oct. 20, 2015.

U.S. Appl. No. 13/744,730, filed Jan. 18, 2013; inventors Troy et al.
U.S. Appl. No. 13/921,246, filed Jun. 19, 2013; inventors Troy et al.
U.S. Appl. No. 13/975,599, filed Aug. 26, 2013; inventors Sarr et al.

* cited by examiner

AUTOMATED SCANNING SYSTEMS FOR NON-DESTRUCTIVE INSPECTION OF CURVED CYLINDER-LIKE WORKPIECES

BACKGROUND

This disclosure generally relates to non-destructive inspection equipment and methods, and relates more particularly to methods and apparatus for inspecting barrel-shaped structures made of composite material.

Non-destructive inspection (NDI) of structures involves thoroughly examining a structure without harming the structure or requiring significant disassembly. Inspection may be performed during manufacturing of a structure and/or after a structure has been put in service to determine the condition, quality, or structural state of the structure.

The production manufacturing of a large composite structure for an active airplane program needs to be done at a rate that meets schedule commitments. Non-destructive inspection of primary structure is a necessary part of the manufacturing process and must be done at a rate capable of keeping up with the published schedule.

For example, it is known to fabricate barrel-shaped fuselage sections made of composite material on an assembly line with high through-put. The finished fuselage sections need to undergo NDI at a high rate. Some existing solutions for inspecting barrel-shaped fuselage sections are large, expensive multiple-axis robotic systems which move ultrasonic transducer arrays over the outer mold line (OML) of the fuselage section using encoded rails and end effectors guided to follow pre-programmed paths.

In addition, high-speed non-destructive inspection of stiffeners (stringers) on the inside of many composite airplane fuselage sections is desirable in order to maintain the manufacturing rate. One existing solution involves rolling the barrel-shaped fuselage section in a rotating tool frame that allows each stiffener being inspected to be under a robotic crawler, so gravity is not an issue, and the stiffener crawlers holding multiple ultrasonic transducer (UT) arrays can crawl on a relatively horizontal surface.

There is a need for improvements in systems and methods for non-destructive inspection of barrel-shaped workpieces (such as fuselage sections that may include internal stiffening elements) that facilitate a high rate of production.

SUMMARY

The subject matter disclosed herein is directed to systems and methods for high-speed non-destructive inspection of a curved cylinder-like workpiece (e.g., in the shape of a half or full barrel). The curved cylinder-like workpiece may be a large-scale part, thereby taking advantage of automation provided by embodiments disclosed herein. Given by way of non-limiting example for illustration purposes only, the curved cylinder-like workpiece may be an aircraft part, such as a barrel-shaped section of an aircraft fuselage. It should be appreciated, however, that the systems and methods described hereinafter with reference to a fuselage section may also be applied to other types of curved cylinder-like workpieces. Furthermore, the curved cylinder-like workpiece need not be related to an aircraft, and can be a part of some other type of vehicle or structure.

Moreover, the curved cylinder-like workpiece may be made of any material as desired for a particular application. It will be appreciated that the type of material used for the curved cylinder-like workpiece may, in part, determine which type of non-destructive inspection technique is used to inspect the curved cylinder-like workpiece. Given by way of non-limiting examples, the curved cylinder-like workpiece may be made of composite material, such as a composite laminate made of fiber-reinforced plastic, or a metal, such as aluminum or titanium. It will be understood that it is not intended to limit in any manner whatsoever the materials from which the curved cylinder-like workpiece may be made.

Depending on the type of material being inspected, any one of a multiplicity of types of NDI sensors can be utilized. A variety of types of NDI sensors suitable for use with the scanning apparatus disclosed herein are listed and described in U.S. Pat. No. 7,743,660 entitled "System and Method for Automated Inspection of Large-Scale Part".

In accordance with some embodiments disclosed herein, the NDI sensor units are supported by apparatus that travels along tracks. As used herein, the term "tracks" encompasses rails, grooves, guide surfaces, and equivalents thereof. A track may be straight (i.e., linear) or curved. For example, for externally scanning a workpiece that extends longitudinally and circumferentially, an NDI sensor unit may be mounted to a carriage that travels circumferentially along a curved track formed by guide surfaces, which curved track in turn is mounted to an arch frame that travels longitudinally along linear tracks in the form of rails.

For the sake of illustration, systems and methods for high-speed ultrasonic inspection of stiffened barrel-shaped (e.g., half or full barrel) fuselage sections made of composite material will be disclosed in detail. However, it should be appreciated that the apparatus disclosed herein can be employed in the non-destructive inspection of barrel-shaped workpieces other than fuselage section using NDI sensor units other than UT arrays.

In the context of the specific application of inspecting fuselage sections, the scanning system may comprise means for scanning the skin of the fuselage section from a vantage point external to the fuselage section and means for scanning substructure, such as stringers attached to the inside of a stiffened fuselage section. The means for scanning the stiffeners on the inside of a fuselage section can work in concert and concurrently with the means that scan the fuselage section externally. In the alternative, the external and internal scanning can be performed at different times and/or at different places. The fuselage sections can be scanned externally before or after the stiffeners have been attached. In the embodiments disclosed below, the scanning means comprise multiple linear UT arrays that collect wide swaths of ultrasonic data. In one configuration, some UT arrays sweep the outer mold line of the fuselage section circumferentially, while other UT arrays travel longitudinally along the length of the stiffeners attached to the inside of the fuselage section.

In accordance with some embodiments, the fuselage sections (or other workpieces) can be scanned externally using a mobile (e.g., translating) arch gantry system comprising a translatable arch frame disposed outside the fuselage section, a carriage that can travel along a curved track carried by the arch frame, a radially extending telescopic arm having a proximal end fixedly coupled to the carriage, and an NDI sensor unit coupled to a distal end of the telescoping arm. The stiffeners of the fuselage sections can be scanned using a mobile scanner platform disposed inside the fuselage section, which platform comprises a radially extending telescopic arm rotatably coupled to a mobile (e.g., holonomic or linear motion) platform and an NDI sensor unit coupled to a distal end of the telescoping arm. The scan data is matched with position data acquired using any one of a plurality of tracking systems to enable the display of NDI features/flaws on a three-dimensional representation of the workpiece.

For fuselage sections having a half barrel shape, the entire OML of the half-barrel fuselage section can be scanned externally using an arch gantry system by moving the latter in increments from one end of the fuselage section to the other end, stopping after each incremental advance to perform a circumferential scan of a respective swath of the fuselage section. In one embodiment for scanning of fuselage sections having a full barrel shape, one half of the full-barrel fuselage section can be scanned externally from one end to the other; then the fuselage section is rotated 180 degrees about its longitudinal axis in the arch gantry system and then the other half of the fuselage section can be scanned externally from one end to the other.

One aspect of the subject matter disclosed in detail below is a method for scanning a workpiece having a curved section that extends longitudinally and circumferentially, the method comprising: (a) moving a curved track along first and second linear tracks to a first longitudinal position, the curved track in the first longitudinal position being disposed radially outward from the curved section of the workpiece; (b) adjusting a position of an NDI sensor unit relative to a carriage to which the NDI sensor unit is adjustably coupled by an extendible arm, the carriage in turn being movable along the curved track; (c) moving the carriage along the curved track while the curved track is stationary at the first longitudinal position; (d) during step (c), activating the NDI sensor unit to inspect a first strip-shaped area of the curved section of the workpiece; (e) processing signals output from the NDI sensor unit to derive a first strip of scan data characterizing a structural state of the first strip-shaped area of the curved section of the workpiece; (f) during step (c), acquiring location data representing locations of the NDI sensor unit relative to the workpiece; and (g) mapping the first strip of scan data to a three-dimensional model of the workpiece based on the location data acquired in step (f). The workpiece may be a fuselage section made of composite material. The method may further comprise displaying features overlaid on a representation of a portion of the three-dimensional model of the workpiece based on the results of steps (e) and (g). The method may further comprise the following steps: (h) subsequent to step (c), moving the curved track along the first and second linear tracks from the first longitudinal position to a second longitudinal position, the curved track in the second longitudinal position being disposed radially outward from the curved section of the workpiece; (i) moving the carriage along the curved track while the curved track is stationary at the second longitudinal position; (j) during step (i), activating the NDI sensor unit to inspect a second strip-shaped area of the curved section of the workpiece; (k) processing signals output from the NDI sensor unit to derive a second strip of scan data characterizing a structural state of the second strip-shaped area of the curved section of the workpiece; (I) during step (i), acquiring location data representing locations of the NDI sensor unit relative to the workpiece using the location tracking system; and (m) mapping the second strip of scan data to the three-dimensional model of the workpiece based on the location data acquired in step (I).

Another aspect is a system for external scanning of a workpiece having a curved outer mold line, the system comprising: first and second linear tracks which are mutually parallel; a curved track disposed in a plane generally transverse to the first and second linear tracks, the curved track being coupled to and translatable along the first and second linear tracks; a carriage coupled to and movable along the curved track; an extendible arm having a proximal end coupled to the carriage; an NDI sensor unit coupled to a distal end of the extendible arm; a location tracking system capable of tracking the location of the NDI sensor unit relative to the workpiece; a data processing system capable of receiving scan data from the NDI sensor unit and location tracking data from the location tracking system and then correlating the scan data with the location tracking data; and a display system capable of displaying the scan data on a three-dimensional representation of the workpiece (such as with texture maps) based on results of the correlating process performed by the data processing system.

A further aspect is a system for scanning a workpiece having a curved section that extends longitudinally and circumferentially, the system comprising: a pair of linear tracks parallel to a longitudinal direction; an arch frame that extends circumferentially and is arranged to travel along the linear tracks; a first actuator which, when activated, causes the arch frame to travel along the linear tracks; a curved track supported by the arch frame; a carriage arranged to travel along the curved track; a second actuator which, when activated, causes the carriage to travel along the curved track; an extendible arm comprising a first member mounted to the carriage and a second member which is arranged to translate relative to the first member; a third actuator which, when activated, causes the second member to translate relative to the first member; and an NDI sensor unit mounted to the second member and operable to acquire scan data during its motion.

Yet another aspect of the disclosed subject matter is a system for scanning a substructure of a curved cylinder-like workpiece, which substructure extends along an inner surface of the workpiece. The system comprises: a mobile platform comprising a frame; a first actuator which, when activated, exerts a force urging the mobile platform to move; an extendible arm comprising a first member pivotably mounted to the frame of the mobile platform and a second member which is translatable relative to the first member; a second actuator which, when activated, exerts a force urging the second member to translate relative to the first member; and a first NDI sensor unit coupled to a distal end of the extendible arm; an encoder device capable of outputting signals representing incremental movements of the first NDI sensor unit along a substructure; and a computer system programmed to perform the following operations: controlling the first and second actuators and the first NDI sensor unit; receiving signals from the encoder device; converting signals from the encoder device into position data representing a position of the first NDI sensor unit along the substructure; receiving scan data from the first NDI sensor unit; and correlating the scan data with the position of the first NDI sensor unit along the substructure. The mobile platform may further comprise a plurality of omnidirectional wheels rotatably coupled to the frame or a plurality of rollers rotatably coupled to the frame which roll on linear tracks.

A further aspect is a system for scanning a stiffened curved cylinder-like workpiece, the system comprising: first means for circumferentially scanning an outer mold line of the workpiece; and second means for scanning a longitudinal stiffener attached to an inner mold line of the workpiece, wherein the first and second means work in concert and concurrently. The system may further comprise an arch frame disposed outside the workpiece and comprising a curved track, the arch frame being translatable along a longitudinal axis of the workpiece, wherein the first means comprise: a carriage that can travel along the curved track;

a radially extending telescopic arm having a proximal end fixedly coupled to the carriage; and an NDI sensor unit coupled to a distal end of the telescoping arm. In addition, the system may further comprise a mobile scanner platform disposed inside the workpiece, wherein the second means comprise: a radially extending telescopic arm rotatably coupled to the mobile scanner platform; and an NDI sensor unit coupled to a distal end of the telescoping arm.

Other aspects of systems and methods for NDI scanning of a curved cylinder-like workpiece with and without longitudinal stiffeners are disclosed below.

BRIEF DESCRIPTION OF THE DRAWINGS

Drawings representing views of physical structures are not drawn to scale. Also, it should be noted that the drawings representing physical structures do not show the flexible cables which electrically connect the hardware to a computer system (not shown) and, in the case of ultrasonic inspection, which connect an ultrasonic transducer inspection unit to a source of acoustic couplant (e.g., water).

Reference will hereinafter be made to the drawings in which similar elements in different drawings bear the same reference numerals.

DETAILED DESCRIPTION

Embodiments of apparatus and methods for non-destructive inspection of curved cylinder-like workpieces in the form of half- or full-barrel-shaped sections of an aircraft fuselage will now be described in detail for the purpose of illustration. The apparatus and methods disclosed herein may also be used for similar applications which require non-destructive inspection, including other curved cylinder-like workpieces. For example, such workpieces may comprise shells or half-shells having a curved cross-sectional profile (e.g., an oval, ellipse, or circle, or any section thereof) that is constant or varies smoothly in a longitudinal direction.

Figure 1:
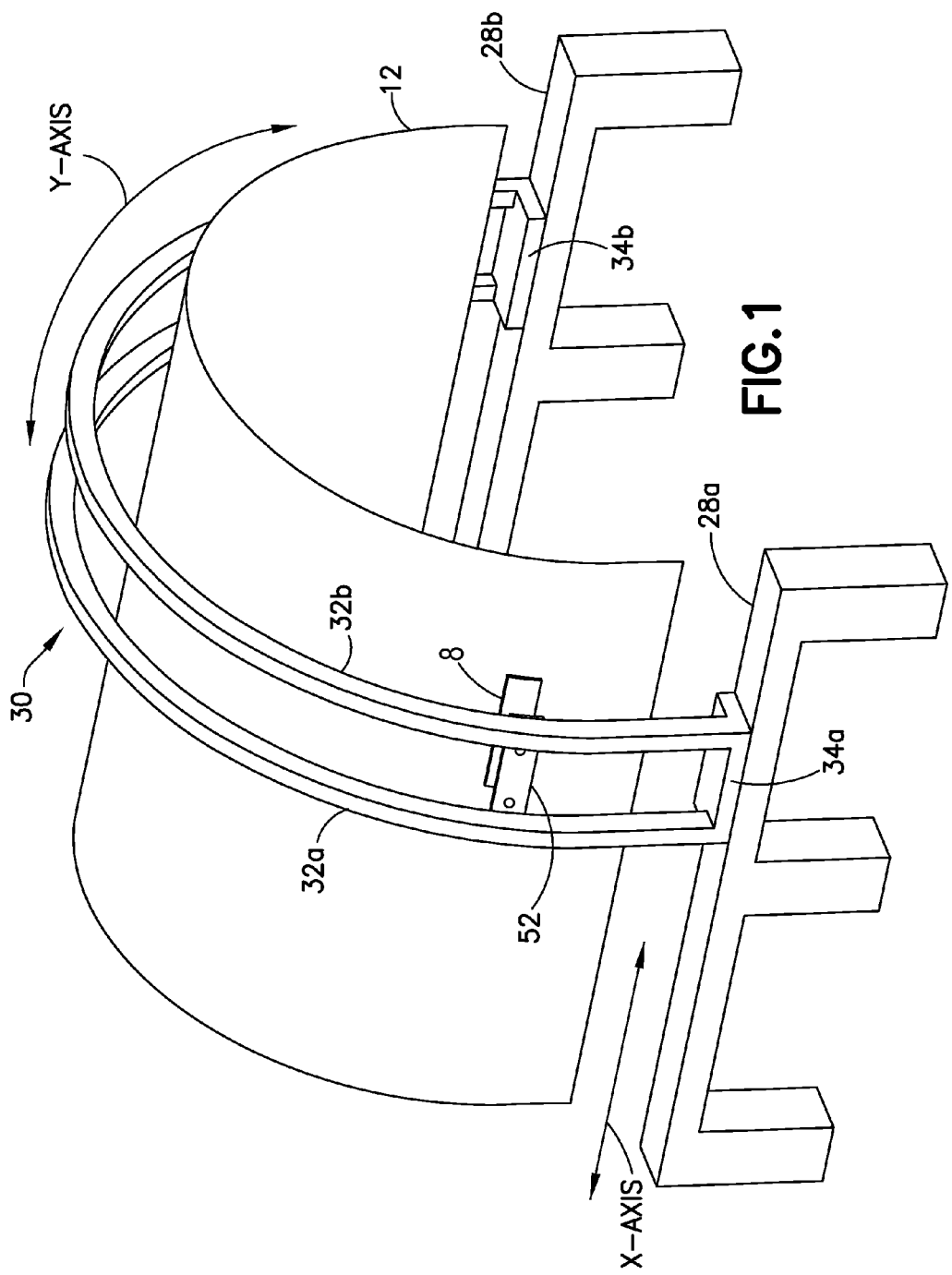
FIG. 1 is a diagram representing an isometric view of portions of an external scanning system for non-destructive inspection of the OML of a fuselage section in accordance with one embodiment.

FIG. 1 represents an isometric view of portions of an external scanning system for ultrasonic inspection of the OML of a half-barrel fuselage section 12 in accordance with one embodiment. (The same external scanning system can be adapted to inspect respective halves of the OML of a full-barrel fuselage section.) Means for supporting the half-barrel fuselage section 12 are not shown in FIG. 1.

During ultrasonic inspection, an NDI sensor unit 8 is scanned circumferentially (i.e., along a Y-axis) across the OML of the half-barrel fuselage section 12 at successive longitudinal positions (i.e., spaced along an X-axis). In the embodiments disclosed herein, the NDI sensor unit 8 takes the form of multiple ultrasonic transducer (UT) elements lined up in an array and contained in a structure called a shoe, mounted to an end effector (not shown), to provide for a wide scan. During each circumferential scan, the NDI sensor unit 8 acquires a respective swath of ultrasound scan data. Successive swaths of ultrasound scan data may be acquired from successive contiguous segments of the half-barrel fuselage section 12 to provide full scan coverage from one end of the half-barrel fuselage section 12 to the other end.

In accordance with the embodiment depicted in FIG. 1, the NDI sensor unit 8 is supported by a translatable arch gantry system 30 comprising a pair of arch frame members 32*a*, 32*b* connected at their opposing ends to gantry trolleys 34*a* and 34*b*. The gantry trolleys 34*a* and 34*b* ride on linear rails (not shown in the drawings) of respective rail assemblies 28*a* and 28*b*. In one implementation, the gantry trolleys 34*a* and 34*b* may comprise rollers that roll along the linear rails. Alternatively, other systems for guiding linear motion could be employed. For example, the gantry trolleys 34*a* and 34*b* may be equipped with sliders comprising respective pairs of recirculating ball bearings that roll along a pair of linear guide tracks. Optionally, the X position of each gantry trolley 34*a*, 34*b* can be measured by a respective position sensor (e.g., an encoder) to provide feedback to a trolley motion control subsystem (not shown in FIG. 1) which controls the X-direction motion of the arch gantry system 30. The half-barrel fuselage section 12 is positioned so that its longitudinal axis (not shown in the drawings) will be parallel to the X axis.

The arch frame members 32*a* and 32*b* are provided with mutually parallel curved tracks (not visible in FIG. 1) preferably disposed in planes transverse to the linear rails of rail assemblies 28*a* and 28*b*. The NDI sensor unit 8 may be coupled to a carriage 52 which is designed to travel along the curved tracks. As the carriage 52 travels along the curved tracks (while the arched gantry system 30 is stationary), the NDI sensor unit 8 can be activated to scan a circumferential portion of the OML of the half-barrel fuselage section 12 from one side edge to the other side edge. The curved tracks may be constructed so that their curvatures approximate the curvature of the workpiece, with a compliant end effector compensating for slight to moderate curvature mismatch. The curvature of the half-barrel fuselage section 12 may be circular, elliptical, oval, or some other shape.

In accordance with one embodiment, the carriage 52 may comprise respective motorized trolleys which travel along the curved tracks of the arch frame members 32*a* and 32*b*, thereby scanning the NDI sensor unit 8 circumferentially across the OML of the half-barrel fuselage section 12. In some embodiments, after each complete pass over the full half-circumference of the half-barrel fuselage section 12, the extendible arm 62 is retracted to lift the NDI sensor unit 8 from the surface and returned to its starting position along the arch frame members 32*a* and 32*b*. In other embodiments, the extendable arm 62 is shifted over to the location of the next strip without retracting and returning to its starting position. This allows the NDI scanning process to run in the opposite direction (saving time by scanning on the return trip). At the same time, the arch gantry system 30 is automatically moved along the X-axis by a distance equal to the width of the swath of scan data acquired. This process is repeated until the entire OML of the half-barrel fuselage section 12 has been scanned. Then the half-barrel fuselage section 12 is removed and the next half-barrel fuselage section is placed in position for external scanning (or in some embodiments, the interior is scanned by another system before the barrel is moved out). In the case of external scanning of a full-barrel fuselage section, first one half of the full barrel is scanned; then the full barrel is rotated 180 degrees and the other half is scanned. Then the full barrel is removed and a next full-barrel fuselage section is placed in position for external scanning.

In the alternative, two or more arch gantry systems of the type shown in FIG. 1 can be mounted to the rail assemblies 28*a* and 28*b* for scanning respective portions of the half-barrel fuselage section 12 concurrently. By operating multiple NDI sensor units concurrently, the rate of inspection can be increased.

Figure 2:
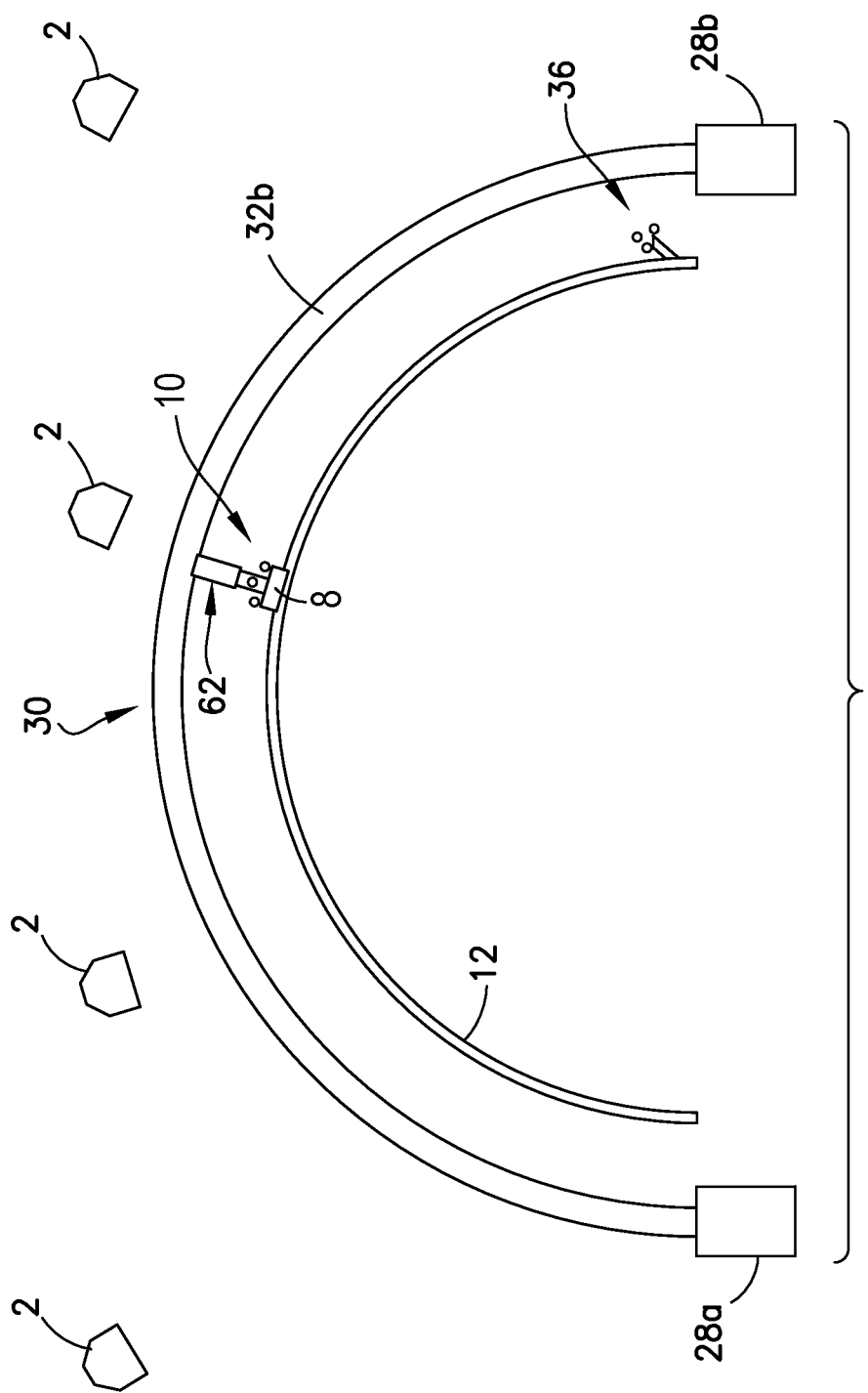
FIG. 2 is a diagram representing an end view of portions of an external scanning system having an NDI sensor unit whose location is tracked by a motion capture system.

FIG. 2 is an end view of portions of an external scanning system of the type shown in FIG. 1 wherein the location of the NDI sensor unit 8 is tracked using a motion capture system. (As in FIG. 1, the means for supporting the half-barrel fuselage section 12 are not shown in FIG. 2.) The NDI sensor unit 8 can be coupled to the carriage (not visible in FIG. 2) by means of an extendible arm 62. The extendible arm 62 may be in a retracted position during longitudinal movement of the arch gantry system 30. Prior to initiation of a circumferential scanning operation, the extendible arm 62 can be actuated to extend, bringing the shoe of the NDI sensor unit 8 into contact with the OML of the fuselage section 12. (In alternative applications of the scanning system in which the NDI sensor unit does not include contact-type sensors, the extendible arm may be extended to bring the NDI sensor unit into proximity without contacting the OML of the workpiece.)

The motion capture hardware partly depicted in FIG. 2 may be of the type used in the process disclosed in U.S. patent application Ser. No. 13/744,730 entitled "Motion Capture Tracking for Nondestructive Inspection". As seen in FIG. 2, the motion capture system comprises a multiplicity of motion capture cameras 2, a plurality of retro-reflective markers 36 (a.k.a. retroreflectors) attached (temporarily) to the half-barrel fuselage section 12, and a plurality of retro-reflective markers 10 attached to the shoe of the NDI sensor unit 8. Other components of the motion capture system will be described later with reference to FIG. 5. Initially, the motion capture system is turned on and correlated to the optical targets on the shoe of the NDI sensor unit 8. Then the motion capture system can be used to correlate the location of the NDI sensor unit 8 with the collected ultrasound scan data.

During external ultrasonic inspection of a fuselage section, typical NDI scanner software is capable of processing X and Y position data in the form of respective sets of quadrature pulses (X and Y). As will be explained in detail below with reference to FIG. 5, the motion capture system uses a simulated X and Y encoder pulse method (using a separate data acquisition device to generate the pulses) as described in U.S. patent application Ser. No. 13/744,730 (cited above) and in U.S. patent application Ser. No. 13/470,125 entitled "Automated Inspection of Spar Web in Hollow Monolithic Structure". Overall, this would give better absolute positioning data than using encoder wheels, since encoder wheels on occasion are susceptible to slippage.

Full 3-D precision positioning information can be provided by a real-time motion capture system of the type disclosed in U.S. patent application Ser. No. 13/744,730. The scan data can then be overlaid onto a 3-D model of the half-barrel fuselage section 12, so the scan data can be tied to geometry and particularly to stringer locations and features.

Figure 3:
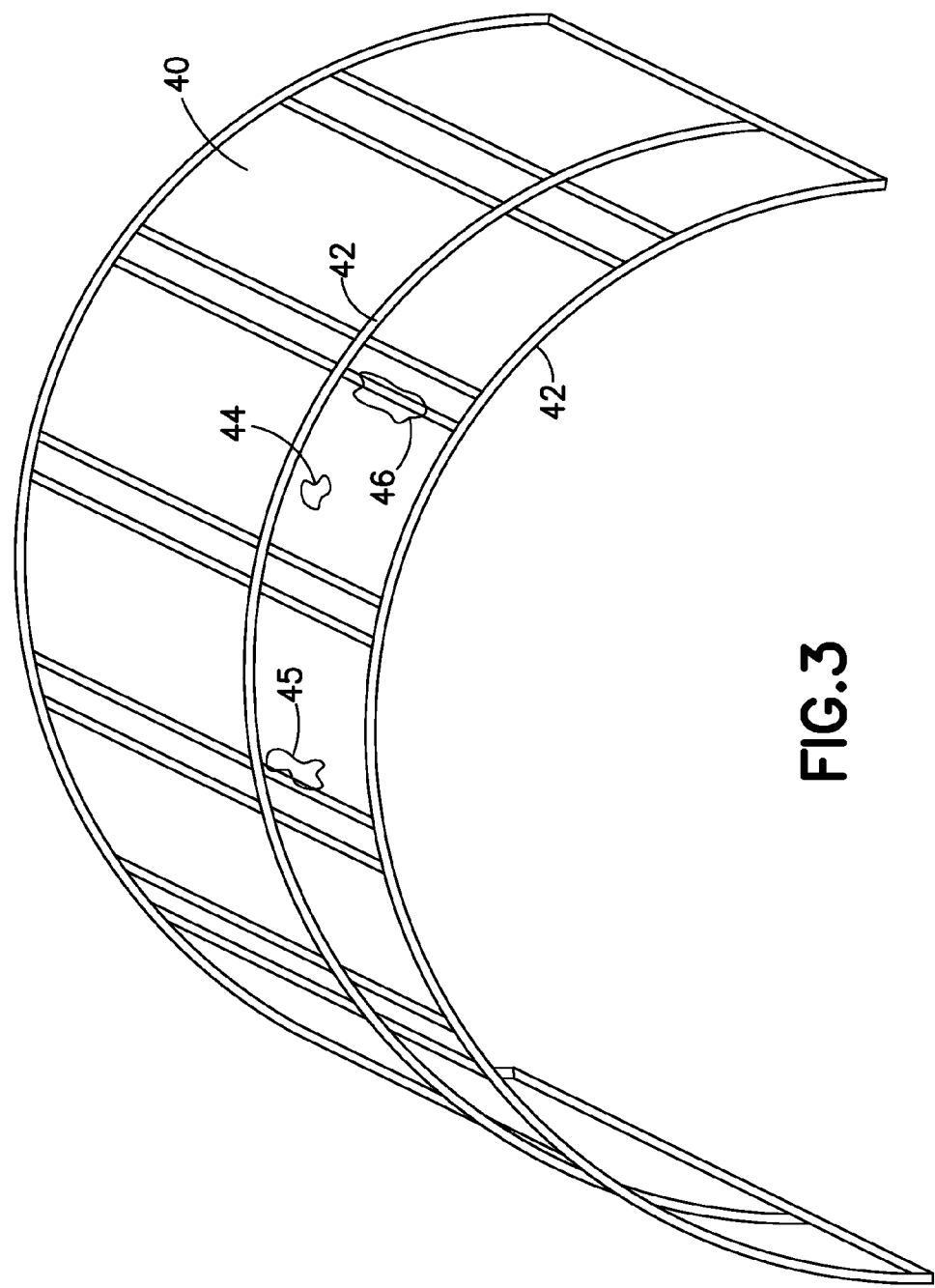
FIG. 3 is a diagram representing a direct three-dimensional (3-D) overlay of NDI data onto a 3-D model of a half-barrel fuselage section.

FIG. 3 is a diagram representing a direct 3-D overlay of strips 42 of scan data onto a 3-D model 40 of a half-barrel fuselage section 12. In one implementation, the NDI sensor unit 8 acquires a respective strip 42 of scan data (comprising returned ultrasound echo signal amplitude and time-of-flight) during each circumferential scan. At the same time, the motion capture system acquires motion/position data which is already in 3-D space that maps directly onto the 3-D model 40 of a half-barrel fuselage section 12. This allows the respective scan strips 42 to be mapped precisely onto the 3-D model 40 of a half-barrel fuselage section 12. The overlay of scan data with the 3-D model 40 enables improved data analysis and potential automated data analysis as well. For example, features/flaw indications 44 and 45 can be directly correlated to the fuselage structure by direct overlay of scan data on the 3-D model. In addition, the direct data overlay onto the model can be used to determine the thickness of a local part 46, which is needed for porosity quantification. In one embodiment, the process involves application of NDI scan data strips as one or more computer graphics texture maps, which are projected onto the 3-D model surfaces in the virtual environment.

Figure 4:
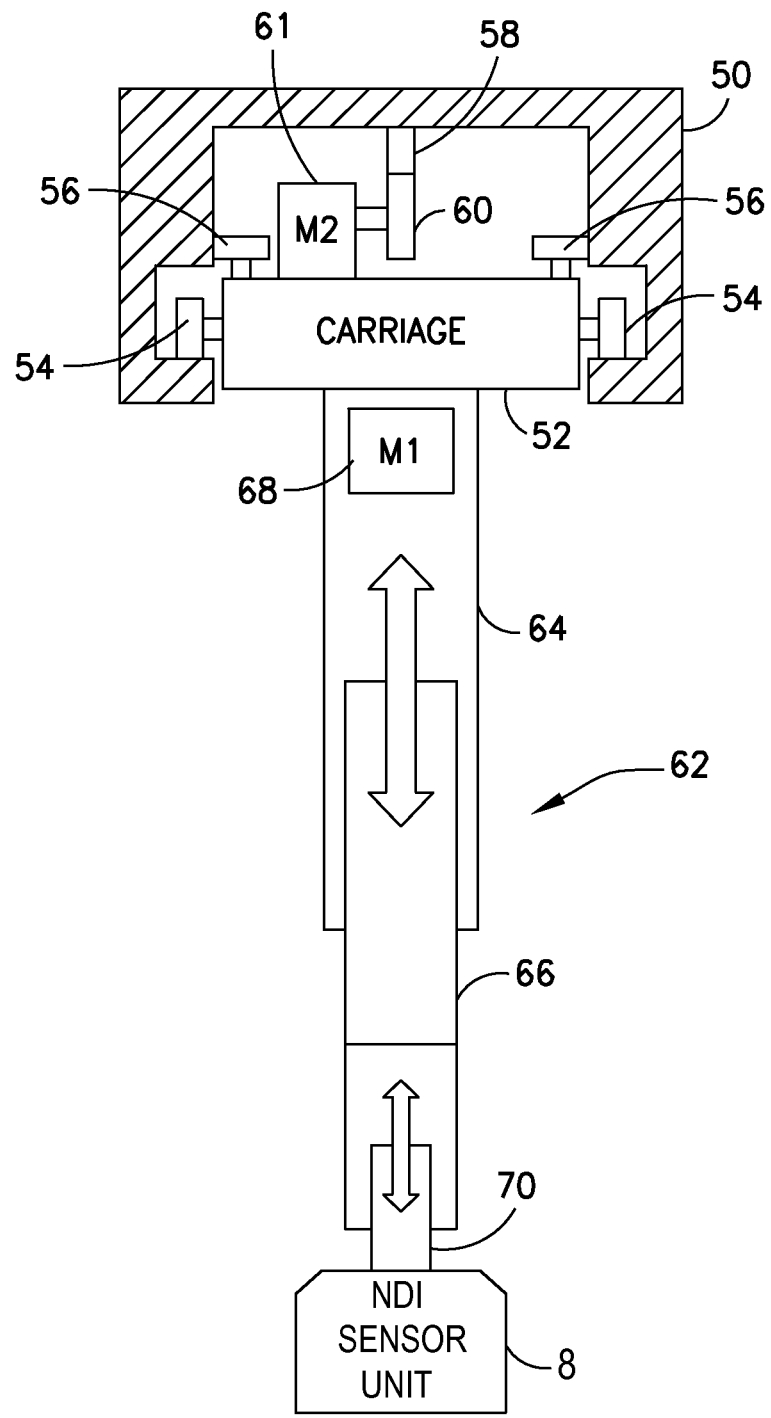
FIG. 4 is a diagram representing an elevational view of an NDI scanning assembly designed to sweep circumferentially along an arch frame of a mobile arch gantry system in accordance with an alternative embodiment.

FIG. 4 is a diagram representing an elevational view of an NDI scanning assembly designed to sweep circumferentially along an arch frame 50 of a mobile arch gantry system in accordance with an alternative embodiment. The arch frame 50 may be constructed to provide guide surfaces for guiding the motion path of a carriage 52 that carries a NDI sensor unit 8. In the implementation depicted in FIG. 4, the carriage 52 may be provided with a first set of rollers 54 (only two of which are visible in FIG. 4) which roll along respective inner circumferential guide surfaces of the arch frame 50 and a second set of rollers 56 (only two of which are visible in FIG. 4) which roll along respective vertical guide surfaces of the arch frame 50. Optionally, a third set of rollers may be provided which roll along respective outer circumferential guide surfaces of the arch frame 50. The carriage 52 will follow a generally circumferential path as it travels along the curved tracks formed by the guide surfaces. In the alternative, arched frame could be constructed with curved rails and the carriage 52 could be provided with diametral sets of rollers which roll along the respective curved rails (in a manner similar to the rollers 132 which roll along linear rails 130*a*, 130*b* depicted in FIG. 12, to be described in detail later).

The NDI scanning assembly shown in FIG. 4 further comprises circumferential motion actuator in the form of a motorized rack and pinion subsystem. This rack and pinion subsystem comprises a curved rack 58 attached to the arch frame 50 and a pinion gear 60 having teeth which interengage the teeth of curved rack 58. The guide surfaces that guide rollers 54 and the curved rack 58 may be semi-circular and mutually concentric. However, the curvature of the guide surfaces that guide rollers 54 and the curved rack 58 may vary from semi-circular depending on the shape of the OML of the fuselage section being inspected.

In accordance with the implementation shown in FIG. 4, the pinion gear 60 is mounted to an end of an output shaft of a stepper motor 61 that is mounted to the carriage 52. Rotation of pinion gear 60 causes the carriage 52 to travel along the curved tracks, during which the NDI sensor unit will be scanning the OML of the fuselage section circumferentially. In the alternative, other known circumferential motion actuators could be employed, such as a cable system capable of pulling the carriage in one direction or in an opposite direction.

Still referring to FIG. 4, the NDI scanning assembly may further comprise an extendible arm 62 in the form of a telescoping arm comprising an outer sleeve 64 attached to the carriage 52 and an inner sleeve 66 which is axially translatable inside the outer sleeve 64. Linear motion of the inner sleeve 66 can be actuated via hydraulics, pneumatics, or a motor turning a threaded screw. In the embodiment shown in FIG. 4, the linear motion actuator comprises a lead screw (not shown) coupled to the output shaft of a motor 68 (for example, a stepper motor) and threadably coupled to a nut (not shown) attached to the inner sleeve 66. In response to activation of motor 68, the inner sleeve 66 and the NDI sensor unit 8 coupled to inner sleeve 66 can be extended or retracted, to allow the operator to set the nominal length or retract the arm during insertion of the fuselage section.

In accordance with a further feature, the NDI sensor unit 8 can be spring loaded to account for variation in the external surface of the fuselage section. More specifically, the NDI sensor unit 8 can be coupled to the inner sleeve 66 by means of a compliant support structure 70 that both urges the shoe of the NDI sensor unit 8 toward the OML of the fuselage section and flexes to allow the NDI sensor unit 8 to adjust its radial position to take into account variations in the OML of the fuselage section and minor misalignments. For example, the compliant support structure 70 may take the form of flexible couplings. In accordance with one implementation, each flexible coupling may take the form of an aluminum rod having a spiral slot cut through the length of the aluminum tube to form a helical coil in a center section that acts as a spring. The flexure allowed by the center portion of the coupling accommodates angular, parallel and axial misalignment between the extendible arm 62 and the shoe of the NDI sensor unit 8. Such flexible couplings are commercially available from Lovejoy, Inc., Downers Grove, Ill. Further details concerning use of such flexible couplings to provide compliant motion of an ultrasonic transducer array relative to a variable scanned surface can be found in U.S. patent application Ser. No. 13/975,599 entitled "Apparatus for Non-Destructive Inspection of Stringers".

Figure 5:
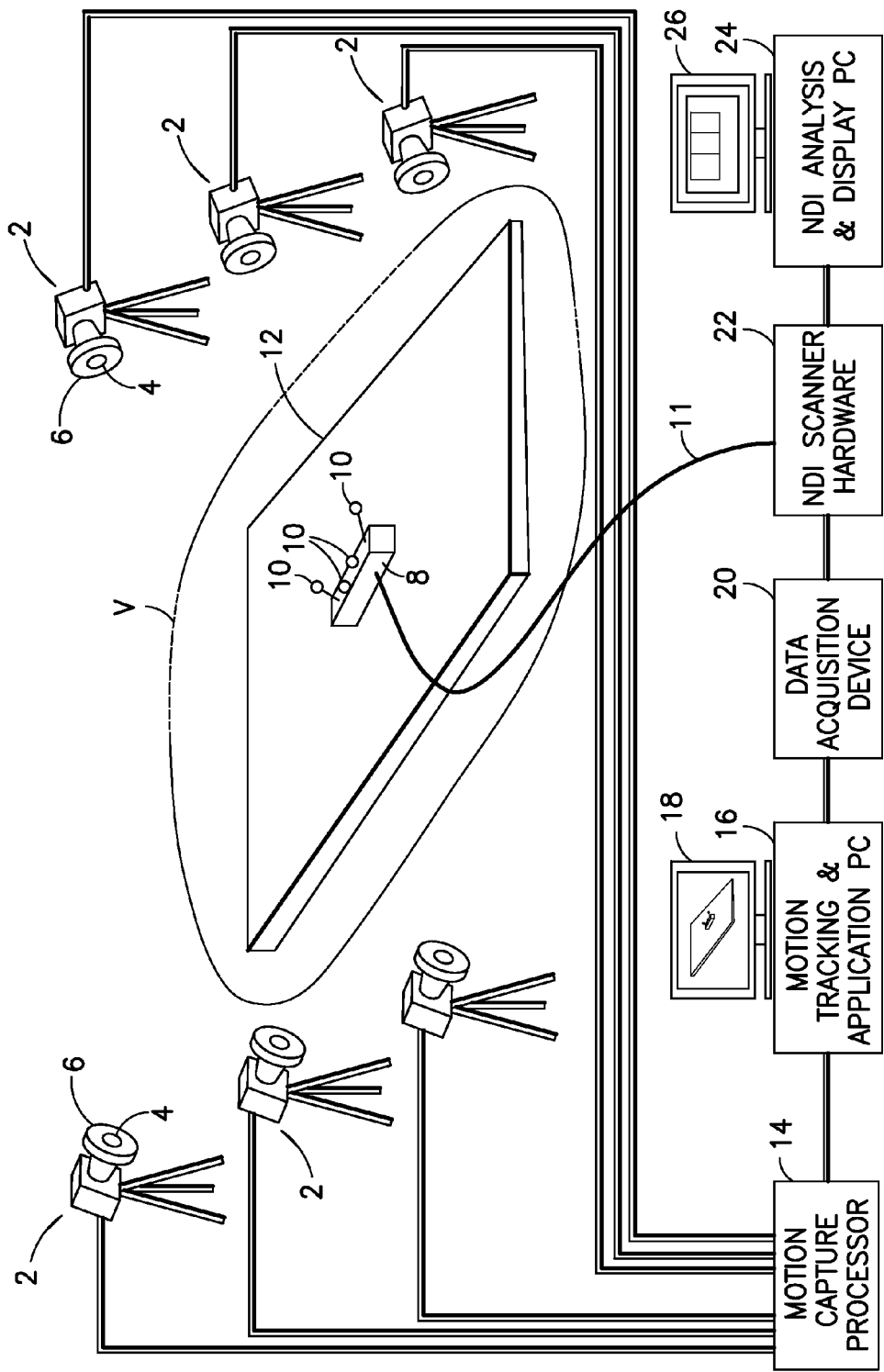
FIG. 5 is a diagram showing a schematic view of a motion capture system for tracking the location of an NDI sensor unit relative the frame of reference of an object (e.g., a workpiece) being scanned in accordance with one embodiment.

FIG. 5 shows a basic system configuration of a motion capture system for tracking the location of an NDI sensor unit 8 relative the frame of reference of a fuselage section 12 (only partially shown in FIG. 5). Multiple motion capture cameras 2 (at least two) are set up around the fuselage section 12 to be scanned to create a three-dimensional capture volume V that captures motion for all six degrees-of-freedom (6-DOF) of the NDI sensor unit 8 being tracked (3-DOF position: x (same as X seen in FIG. 1), y (a first component of Y seen in FIG. 1), z (a second component of Y seen in FIG. 1); and 3-DOF orientation: roll, pitch, yaw). Multiple objects in the capture volume can be tracked simultaneously, e.g., in an inspection scenario where multiple NDI sensor units are scanning the fuselage section 12. Each NDI sensor unit 8 to be tracked has a respective group (at least three) of passive retro-reflective markers 10 attached thereto, the markers of each group being arranged in a respective unique, non-collinear pattern. In the example shown in FIG. 5, the NDI sensor unit 8 has four retro-reflective markers 10. In the case of the embodiment partially depicted in FIG. 2, the fuselage section also has a group of retro-reflector markers 36, which are used by the motion capture system during an alignment procedure that enables a determination of the location of the NDI sensor unit 8 in the frame of reference of the fuselage section 12. In one embodiment, a known marker pattern is placed in a known location on the target object and the alignment offset (position and orientation) between the target object coordinate system and the motion capture coordinate system is determined. The markers of each group are arranged in known patterns, and the information for defining the patterns is stored in the motion capture processor 14. A marker pattern can be defined relative to a specific location on the NDI sensor unit 8 so that the marker pattern origin aligns with the origin of the NDI sensor unit; or in the alternative, the marker pattern can be attached to the NDI sensor unit 8 and then the offset position and orientation between the origin of the marker pattern and the origin of the NDI sensor unit 8 is determined and used in a matrix transformation multiplication. The result from either approach is that the position and orientation of the marker pattern is defined relative to the origin of NDI sensor unit 8.

Each motion capture camera 2 seen in FIG. 5 can be a video camera of the type comprising a ring of LEDs 6 surrounding a camera lens 4. In conjunction with such cameras, each retro-reflective marker 10 may comprise a hemispherical or ball-shaped body coated with retro-reflective paint, that reflects impinging light from the LEDs 6 of each camera 2 back toward the associated lens 4 of the respective camera in a well-known manner (i.e., the reflected light beam is substantially parallel to the transmitted light beam). In one known implementation, the retro-reflective marker comprises a surface coating made of a large number of micro-spheres, each of which are a refracting optical element in the form of a transparent sphere and a reflective surface in the form of a hemi-spherical mirror. The motion capture system utilizes data captured from image sensors inside the cameras 2 to triangulate the three-dimensional position of the NDI sensor unit 8 between multiple cameras configured to provide overlapping projections.

The outputs from cameras 2 are input to respective ports of motion capture processor 14. The motion capture processor 14 collects real-time image information from all of the motion capture cameras 2, processes the image data, and sends the information along a dedicated connection to a motion tracking and applications computer 16, which has a display monitor 18 associated therewith for displaying the processed image data. Alternatively, the software functions executed by motion capture processor 14 and motion tracking and applications computer 16 can be executed by a single computer, i.e., the two hardware components can be integrated inside one enclosure.

At each frame update, the positions of all of the retro-reflective markers 10 in the capture volume V can be captured by each camera 2 and converted by the motion capture processor 14 into three-dimensional coordinates, which are then associated with the known marker pattern attached to the NDI sensor unit 8, resulting in full 6-DOF position and orientation representations for the NDI sensor unit 8. A separate data conversion application running on motion tracking and applications computer 16 accesses this object position/orientation data (also referred to herein as "location data") through a network socket connection to the motion capture processor 16.

The data conversion application transforms the location data into the coordinate system for the NDI scan, and then converts the coordinate data into X and Y quadrature encoder pulse instructions, which adopt the same format as pulses from a commercially available position encoder. The data acquisition device 20 converts the X and Y quadrature pulse instructions into electrical signals that simulate X and Y encoder pulses. These simulated X and Y encoder pulses are sent by the data acquisition device 20 to the NDI scanner hardware 22. In accordance with one embodiment, the data acquisition device 20 is a hardware component that takes pulse instructions (e.g., 1's and 0's from the motion tracking and application computer 16) and converts them into actual electrical pulses at the correct voltage, which pulses are sent over signal wires to the inputs of the NDI scanner hardware 22. In other words, the software running on the motion tracking and applications computer 16 converts location data into simulated quadrature pulse instructions and sends those pulse commands (via a USB connection) to the data acquisition device 20 that generates the simulated quadrature pulse signals.

The simulated X and Y pulse signals are received by an NDI processor of the NDI scanner hardware 22. The NDI processor decodes the simulated X and Y quadrature pulse signals into X-Y position data representing the position of the NDI sensor unit 8 in two dimensions. The NDI processor of the NDI scanner hardware 22 also receives NDI scan imaging data from the NDI sensor 8 via cable 11. The 2-D NDI scan data is then mapped to the 3-D space of the model of the fuselage section using the X,Y,Z coordinates of the location of the end effector from either the motion capture data (described above) or encoder data and forward kinematics computation (described later). Visualization of the 2-D NDI scan data in a 3-D environment may use texture maps projected onto the surface of the 3-D solid models.

In accordance with one embodiment, the NDI scanner hardware 22 is an integrated unit comprising a pulser, a receiver and an electronics box. An NDI processor that is part of the receiver converts the simulated encoder pulses into a current X,Y position in accordance with the formulas:

$$X\_pos = num\_of\_x\_pulses\_received * x\_scale\_factor$$

$$Y\_pos = num\_of\_y\_pulses\_received * y\_scale\_factor$$

where each scale factor is a small number (e.g., on the order of 0.01 inch per pulse). This X,Y position is updated many times per second.

At the same time the NDI sensor unit 8 is capturing inspection data (e.g., scan imaging data). In the case where ultrasonic detection is being utilized, data from each element of a linear array of ultrasonic elements can be acquired. These elements make up an array that is analogous to a row of pixels on a computer monitor (where each row is offset from the next by defining the starting X,Y position of the first pixel and when all the rows are displayed in proper order, a full image can be displayed).

Each time the array is moved a predefined distance, the NDI scanner hardware 22 receives a new strip of scan data from the NDI sensor unit 8 (representing a "row" of pixel data) via cable 11. Each strip of scan data is saved to memory. The NDI software uses the current X_pos and Y_pos data derived from the received pulse data to locate the starting point in the image where to place the row of pixels.

The NDI scanner hardware 22 associates the position data and the scan imaging data. The associated data is then sent to an NDI analysis and display computer 24, which uses the position data and scan imaging data to assemble a two-dimensional image of the object being scanned for display on display monitor 26. In accordance with one implementation, the NDI scanner hardware 22 and the NDI analysis and display computer 24 may be connected components of a phased array acquisition instrument such as the TomoScan FOCUS LT, which is commercially available from Olympus Corporation.

The position data derived from the simulated encoder pulses enables the NDI analysis and display computer 24 to compute and display a final C-scan image. The C-scan presentation provides a plan-type view of the location and size of part features. In the case of ultrasound imaging, the plane of the image is parallel to the scan pattern of the ultrasonic transducer array of the NDI sensor unit. In a C-scan, there is location information shown in the display. The location is found along the horizontal and vertical axes (or rulers) of the NDI data display. Individual pixels make up the C-scan. The width of each pixel directly corresponds to a specific number of pulses, which is defined by the resolution of a simulated dimensional encoder associated with a first axis of the part, while the height of each pixel directly corresponds to a specific number of pulses, which is defined by the resolution of a simulated dimensional encoder associated with a second axis of the part which is perpendicular to the first axis. Operators are able to make area measurements of flaws that might show up in the C-scan.

In an alternative display mode, the 3-D model of the fuselage section, the NDI sensor unit location data, and the scan data can be used to generate the three-dimensional image graphically represented in FIG. 3.

FIG. 5 shows one possible configuration for the system, but other configurations are also possible, such as having the motion capture and application software running on a single computer, or combining the NDI scanning system components into a single device. More details concerning the motion capture process can be found in U.S. patent application Ser. No. 13/744,730.

In accordance with alternative embodiments, the location of the NDI sensor unit 8 (see FIG. 4) can be tracked using positional encoders only that measure incremental movements of: (1) the arch frame 50 along the linear rails; (2) the carriage 52 along the curved tracks of the arch frame 50; and (3) the inner sleeve 66 of the extendible arm 62 relative to the outer sleeve 64. In accordance with one OML scanning implementation, the encoder-based solution (no motion capture) uses three separate linear encoders.

Figure 6:
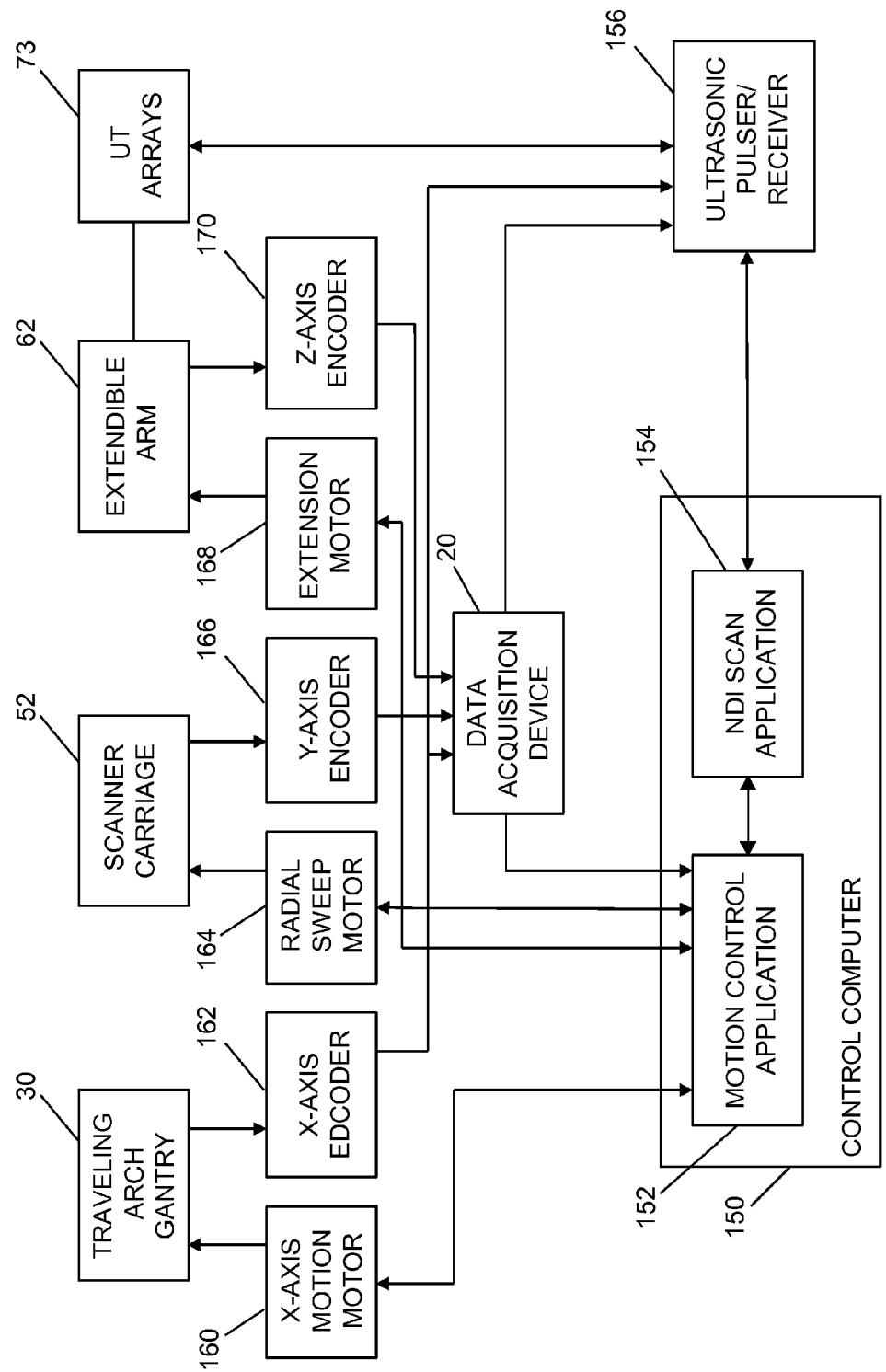
FIG. 6 is a block diagram showing components of a control system in accordance with another embodiment that uses encoders to track the relative location (e.g., relative to an initial location acquired using a local positioning system) of an NDI sensor unit mounted to an external scanning system of the type partly depicted in FIG. 1.

FIG. 6 is a block diagram showing components of a control system that uses rotational or linear encoders to track the relative location (e.g., relative to an initial location acquired using a local positioning system) of an NDI sensor unit mounted to an external scanning system of the type partly depicted in FIG. 1. The control system comprises a ground-based computer 150 programmed with motion control application software 152 and NDI scan application software 154. The control computer 150 is connected to an X-axis motion motor 160 (which drives translation of the arch gantry system 30 along the linear rails), a radial sweep (i.e., Y-axis motion) motor 164 (which drives circumferential movement of carriage 52 along the curved tracks of the arch gantry system 30), and an extension (i.e., Z-axis motion) motor 168 (which drives extension/retraction of the extendible arm 62). The control computer 150 may comprise a general-purpose computer programmed with motion control application software 152 comprising respective software modules for controlling the motors. The motion control application 152 controls the operation of the motors based on position feedback from respective encoders, namely, X-axis encoder 162, Y-axis encoder 166, and Z-axis encoder 170.

The control computer 150 is connected to the motors and encoders via an electronics box (not shown in FIG. 6). The electronic box contains the system power supplies and a data acquisition device 20, and integrates all the scanner control connections and provides an interface between the control computer 150 and respective flexible electrical cables that connect to the gantry, carriage and extendible arm.

Motion control application software 152 controls the extension motor 168 to produce specified radial motion of the UT arrays 73. The range of radial motion of the UT arrays 73 in both directions may be limited by limit switches (not shown). In accordance with one embodiment, the Z-axis encoder 170 measures the angular position of the output shaft of an extension motor 168 that drives rotation of a lead screw, which angular position in turn determines the radial displacement of the ultrasonic transducer arrays 73 effectuated by the extendible arm 62. The motion control application software 152 is thus capable of moving the UT array 73 circumferentially along the OML of the fuselage section being inspected.

In accordance with one embodiment, the encoded data from linear encoders 162, 166 and 170 is received by a data acquisition device 20. The data acquisition device 20 also has digital input and output connections that are used for multiple functions within the system.

Direct use of the X and Y encoder data by the NDI software will give a rough approximation of the surface motion, but not a perfect solution, since the fuselage section will not be perfectly circular. Alternatively, it is possible to use kinematics equations to get an accurate estimation of the surface X-Y translation, assuming the components are not too flexible. The kinematics equations take into account the non-circular shape of the fuselage section. Using this approach requires that the data acquisition device 20 generate simulated encoder pulses. In order to calibrate the encoder-based system, all of the encoders would need to be zeroed in a known location relative to the fuselage section. The data acquisition device may not be necessary for some LPS-plus-encoder embodiments where the fuselage section is circular.

The data acquisition device 20 can be configured to generate simulated quadrature encoder pulses representing incremental Y motion along the OML of the fuselage section. Those simulated encoder pulses are output through digital output ports to an ultrasonic pulser/receiver 156. The ultrasonic pulser/receiver 156 also receives pulses generated by the X-axis encoder 162. The pulser/receiver 156 sends the encoder pulses to the NDI scan application 154. The NDI scan application 154 uses the encoder values to position the scan data in the proper location.

The control computer 150 hosts ultrasonic data acquisition and display software that controls the ultrasonic pulser/receiver 156. The ultrasonic pulser/receiver 156 in turn sends pulses to and receives return signals from the ultrasonic transducer arrays 73. The NDI scan application software 154 controls all details of the scan data and the display of data.

Referring to FIGS. 1 and 2, an exemplary process for externally scanning a fuselage section will now be described. First, the fuselage section 12 is moved into position under the arch gantry system 30. The arch gantry system 30, carriage 52 and extendible arm 62 should be in their respective starting positions. The motion capture system is turned on and correlated to the retro-reflective markers 10 attached to the scan shoe of the NDI sensor unit 8 and to the retro-reflective targets 36 which are temporarily attached to the fuselage section 12. The radial motion actuator is activated so that the NDI sensor unit 8 is moved circumferentially from one side edge of a half-barrel fuselage section 12 to the other side edge. A wide swath of ultrasound scan data, that is slightly less than the width of the multi-array shoe, is collected and stored for analysis. During scanning, the motion capture cameras 2 directed toward the retro-reflective markers 10 precisely track the motion and data location in 3-D space. The ultrasonic scan data is then correlated to a 3-D model of the fuselage section (as shown in FIG. 3) for efficient processing by an analyst. Once the full half-circumference is scanned, the NDI sensor unit 8 is lifted from the external surface of the fuselage section and, in one embodiment, returned to its starting position. In another embodiment, the NDI sensor unit 8 is shifted over and returns on an adjacent path. In addition, the arch gantry system 30 is moved axially along the linear rails to an adjacent location (displaced by the width of the circumferentially scanned area from the previous location). The radial motion actuator is re-activated to collect the adjacent swath of scan data, and this is repeated down the length of the half-barrel fuselage section 12 until the scan is completed. If a full-barrel fuselage section is being scanned, the fuselage section is rotated 180 degrees about the longitudinal (roll) axis and the process is repeated.

The benefits of the external scanning system disclosed above include fast scanning, simple programming, a simple structure, and low maintenance costs. Real-time tracking of the scanner also enables real-time visual indication of the path displayed on a 3-D representation of the half-barrel fuselage section with path trace lines. The moving arch gantry system can also be displayed in real-time. Locations of potential problem areas could be marked visually (and noted in the coordinate system of the fuselage section). Scan plans could be previewed on the 3-D model to confirm the motion plan before starting the actual scan. Also, the control system could be set up to allow the user to select a point on the 3-D model of the full or half barrel and have the arch gantry system move to the selected location.

In addition to scanning the outer mold line of the fuselage section, the stringers of stiffened fuselage sections can be concurrently (or at a different time) scanned using a mobile scanner platform disposed inside the fuselage section. Inspecting hat stringers (i.e., stringers comprising a straight central cap portion, two angled sides connected to the central cap portion by respective cap corners, and two flanges connected to the angled sides by respective flange corners) normally requires a one-sided inspection technique, such as pulse echo ultrasonic (PEU) inspection. The NDI sensor unit can be configured and then strategically placed and oriented to ensure full inspection of the entire hat stringer in one pass. Support structures for inspection sensors, also referred to as shoes, may be fabricated for specific placement and orientation of UT arrays corresponding to the intended shapes and sizes of hat stringers.

In many cases, each hat stringer is a trapezoidal structure comprising angled sides which connect to a cap at respective cap corners. Each hat stringer is affixed to the skin of the fuselage section by respective flanges which connect to the angled sides of the hat stringer at respective flange corners. In order to inspect hat stringers having such a structure, one approach is known using a suite of seven transducer arrays: one to inspect a central cap portion; two to inspect angled sides; two to inspect cap corners; and two to inspect flange corners. It should be understood that the term "corner" as used herein refers to a radiused (i.e., filleted) intersection of surfaces. The central cap portion may be a planar surface connecting the cap corners.

In accordance with the teachings herein, the NDI sensor unit for internal scanning can be designed and configured for inspecting hat stringers, stringers having rounded caps, or stringers having other profiles. For example, for inspecting a hat stringer, the NDI sensor unit may comprise seven UT arrays, whereas for inspecting a rounded cap stringer, only five UT arrays can be employed, as disclosed in U.S. patent application Ser. No. 13/975,599. In either case, the NDI sensor unit can be coupled to the distal end of a pivotable telescoping arm of a computer-controlled manipulator for scanning each stringer in a lengthwise direction (assuming, for the purpose of illustration, that the stringer is straight).

Figure 7A:
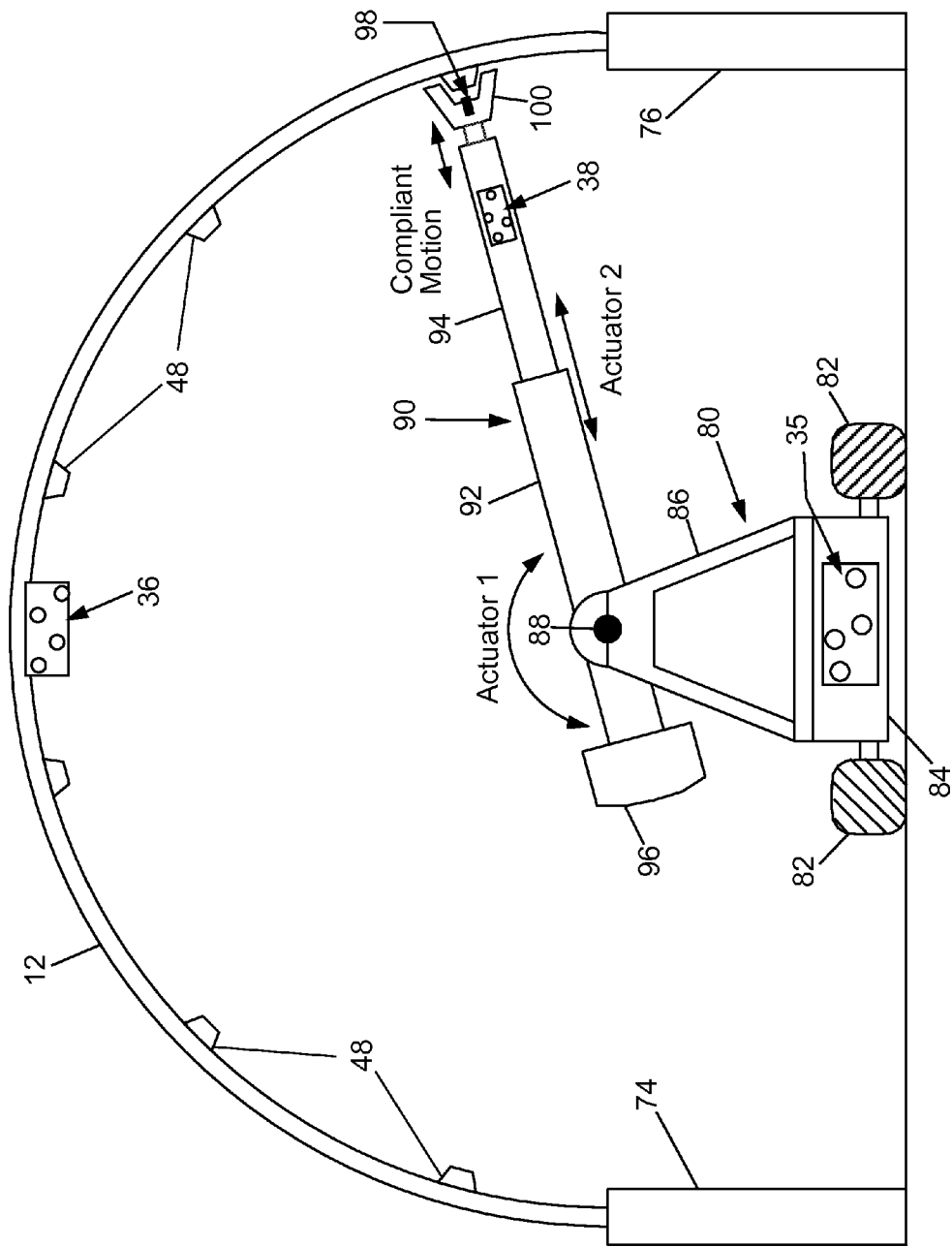
FIG. 7A is a diagram representing an end view of portions of an internal scanning system for scanning stringers of a half-barrel fuselage section, such system having a single arm configuration and comprising a holonomic motion platform with motion capture tracking.

FIG. 7A is a diagram representing an end view of portions of an internal scanning system for scanning stringers 48 of a half-barrel fuselage section 12 in accordance with one embodiment. The side edges of the half-barrel fuselage section 12 are supported by left and right supports 74 and 76 respectively. Although supports 74 and 76 are depicted as fixed structures, in the alternative the fuselage section may be transported into position for inspection by means of automated guided vehicles or other transport devices, with the understanding that the fuselage section is stationary during the internal scanning operation.

The internal scanning system depicted in FIG. 7A comprises an NDI sensor unit 100 coupled to a distal end of an extendible arm 90 which is pivotably coupled to a holonomic motion platform 80. A holonomic system is one that is not subject to motion constraints. As used in this disclosure, a vehicle is considered to be holonomic if the controllable degrees of freedom are equal to the total degrees of freedom. This type of system can translate in any direction while simultaneously rotating. This is different than most types of ground vehicles, such as car-like vehicles, tracked vehicles, or wheeled differential-steer (skid-steer) vehicles, which cannot translate in any direction while rotating at the same time.

In accordance with the embodiment depicted in FIG. 7A, the holonomic motion platform 80 comprises a base 84, four omni (or Mecanum) wheels 82 (only two of which are visible in FIG. 7A) rotatably coupled to the base 84, four motors (not shown, but mounted to the base 84) which respectively actuate rotation of the wheels; a frame 86 attached to the base 84, and a pivot joint 88 supported the frame 86 and connected to the extendible arm 90. The motors onboard the holonomic motion platform 80 can be controlled initially by a system operator during set-up and later by motion control software during scanning. The holonomic motion platform 80 may be controlled to move parallel to a projection of the stringer axis onto the ground. In cases wherein the profile of the fuselage section is constant, the stringers will be parallel to the X-axis (see FIG. 1). In these cases, the NDI sensor unit 100 will travel along the stringer being inspected as the holonomic motion platform 80 is moved in the X-axis direction. The system seen in FIG. 7A further comprises an encoder wheel 98 rotatably coupled to the NDI sensor unit. As the NDI sensor unit 100 scans the stringer and acquires scan data, an encoder (not shown) coupled to the encoder wheel 98 outputs encoder pulses which will be used to correlate the scan data with an axial position of the origin of the NDI sensor unit.

Still referring to FIG. 7A, the extendible arm 90 comprises a pivotable outer sleeve 92 connected to the pivot joint 88, an inner sleeve 94 that is translatable inside the outer sleeve 92, and an NDI sensor unit 100 coupled to the inner sleeve 94 by means of a compliant support structure similar to the compliant support structure 70 previously described in detail with reference to FIG. 4. Such a compliant support structure enables the NDI sensor unit 100 to adjust its radial position in response to variations in the size and shape of the stringer 48 as the NDI sensor unit 100 travels along the length of the stringer. Such compliant motion is indicated by a double-headed arrow in FIG. 7A.

In addition, a counterweight 96 is coupled to one end of the outer sleeve 92 of the extendible arm 90. Optionally, the counterweight 96 may be movable back and forth along the outer sleeve 92 for the purpose of balancing the moments on opposite sides of the pivot joint 88 to achieve a boom arm equilibrium position. As disclosed in U.S. patent application Ser. No. 14/176,169 entitled "Automated Mobile Boom System for Crawling Robots", the counterweight 96 could be moved by a motor-driven, non-backdrivable lead screw 46 that holds the counterweight in place even when power is disrupted. Control of counterweight position could be provided either by direct operator commands or by a computer programmed in accordance with an automatic balancing algorithm. The automated position control is based on feedback of the tilt angle in order to achieve a neutrally balanced telescoping arm. The counterweight motion rate would be sufficient to address static balance or slow changes to the balance point.

To set up the internal scanning system, first the holonomic motion platform 80 is driven to starting location (i.e., position and orientation) on the floor. Then a first actuator (not shown) is activated to pivot the extendible arm 90 to a target tilt angle dependent on the angular position of the stringer to be inspected. (The pivotability of the extendible arm 90 is indicated by a double-headed arrow labeled "Actuator 1" in FIG. 7A.) At the target tilt angle, the inner sleeve 94 of the extendible arm 90 can be extended by a second actuator (not shown) until the NDI sensor unit 100 engages the stringer to be inspected. (The extendability of the extendible arm 90 is indicated by a double-headed arrow labeled "Actuator 2" in FIG. 7A.) Respective encoders can be coupled to the first and second actuators to provide location feedback to the motion control software.

In the embodiment shown in FIG. 7A, the location of the NDI sensor unit 100 can be tracked using a motion capture system of the type previously described with reference to FIG. 5. The motion capture system partly depicted in FIG. 7A comprises a plurality of retro-reflective markers 35 attached the base 84 of the holonomic motion platform 80, a plurality of retro-reflective markers 36 attached (temporarily) to the half-barrel fuselage section 12, and a plurality of retro-reflective markers 38 attached to the inner sleeve 94 of the extendible arm 90. Alternatively, retro-reflective markers 38 may be attached directly to the end effector or NDI sensor unit 100. A motion capture processor (not shown in FIG. 7A) is programmed to compute the respective locations of the holonomic motion platform 80 and extendible arm 90 in the frame of reference of the fuselage section 12. The motion capture system provides continuous absolute coordinate results. Note that for the embodiments that include motion capture (e.g., FIG. 7A), encoders are not required for the basic concept. But, an optional encoder coupled to encoder wheel 98 on the end-effector (as shown in FIG. 7A) may be used if higher resolution is desired.

When the NDI sensor unit 100 is located correctly relative to the stringer to be inspected, the NDI sensor unit is activated. Then the holonomic motion platform 80 is moved in the X-axis direction, causing the NDI sensor unit 100 to travel along the stringer. A swath of ultrasound scan data is acquired as the NDI sensor unit scans over the radii and flats of the stringer and stored for analysis. Small motions of the NDI sensor unit 100 that would not be possible to accurately detect with measurements taken only at the base 84 of the holonomic platform 80 are tracked using the encoder wheel 98, which rotates as the NDI sensor unit 100 travels along the length of the stringer 48 during scanning. For higher resolution, an encoder (not shown) coupled to the encoder wheel 98 outputs encoder pulses that are used to correlate the ultrasound scan data with the axial position of the origin of the NDI sensor unit 100.

Once the entire length of a stringer at a particular radial angle has been scanned, the extendible arm 90 is rotated to the angular position of the next stringer and the above steps are repeated. This procedure is followed until all of the stringers have been scanned.

Figure 7B:
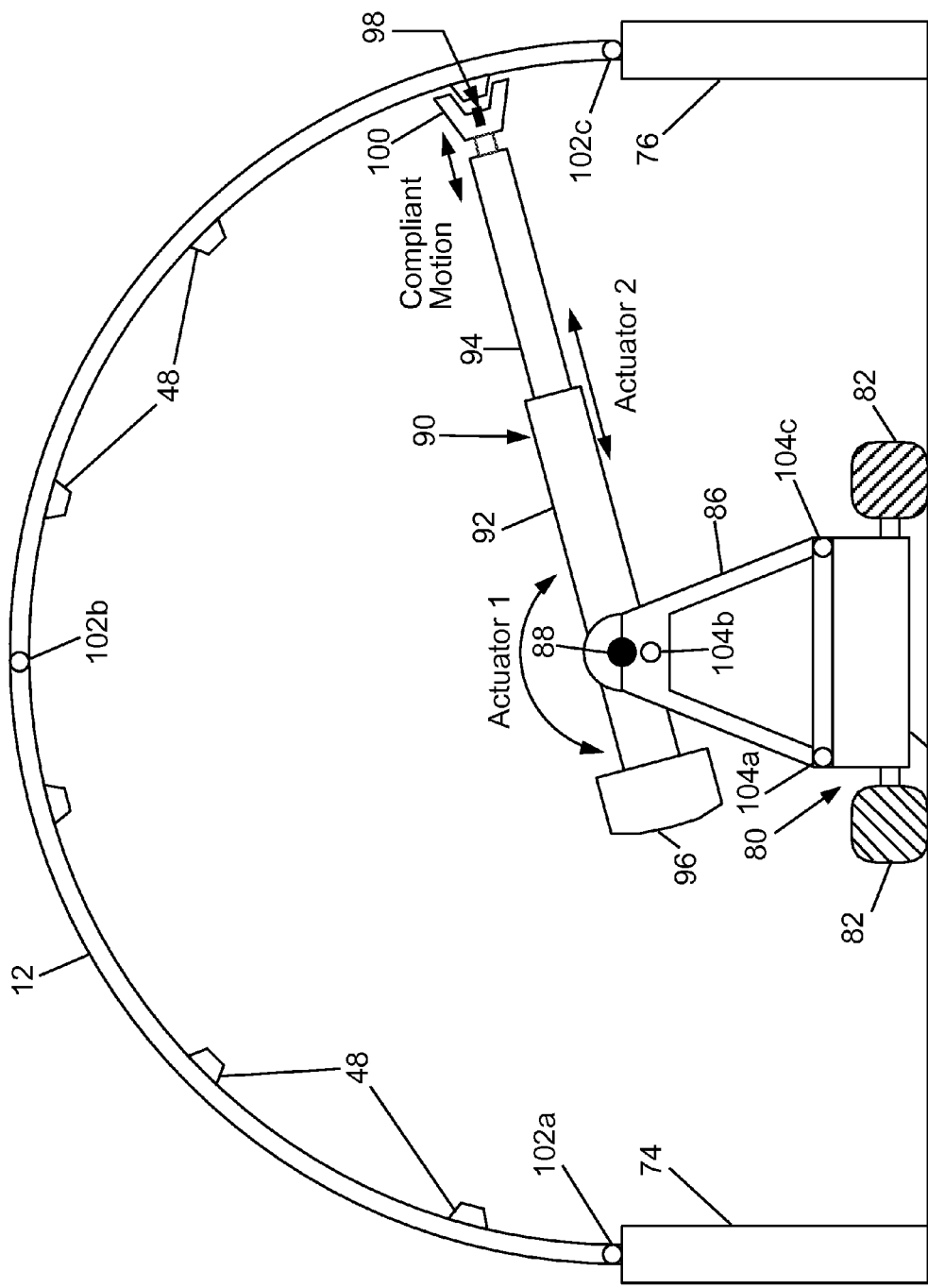
FIG. 7B is a diagram representing an end view of portions of an internal scanning system for scanning stringers of a half-barrel fuselage section, such system having a single arm configuration and comprising a holonomic motion platform with LPS (Local Positioning System) and encoder tracking.

FIG. 7B is a diagram representing an end view of portions of an internal scanning system for scanning stringers of a half-barrel fuselage section that uses LPS tracking instead of motion capture tracking. In accordance with this embodiment, the NDI sensor unit 100 is coupled to a distal end of an extendible arm 90 which is pivotable relative to a holonomic motion platform 80. This hardware configuration may be identical to that described with reference to FIG. 7A.

In the embodiment depicted in FIG. 7B, three calibration points (i.e., optical targets) 102a-102c are temporarily attached to the fuselage section 12, while another three calibration points 104a-104c are attached to the holonomic motion platform 80. These calibration points can be detected using an LPS (not shown in FIG. 7B) of the type disclosed in U.S. Pat. No. 7,859,655. Such an LPS permits an operator to acquire local coordinate measurement and imaging data for an object in the field of view of the physical hardware of the LPS. The LPS may use a pan-tilt unit to orient the instrument (a camera and laser range meter) in the direction of a target object for which local coordinates are needed. The laser range meter can be used to measure range to the object, or distances can be entered or derived algorithmically. Image data, measured range data, and pan-tilt angles are used along with known calibration points to determine the location of the LPS device relative to the target object. With the relative location known, additional LPS measurements are converted into the local coordinates of the target object's coordinate system (such as the coordinate system of the fuselage section 12). More specifically, the LPS disclosed in U.S. Pat. No. 7,859,655 can use known calibration points 102a-102c on the half-barrel fuselage section 12 to perform an instrument-to-target calibration, after which the LPS can be used to measure the coordinates of the calibration points 104a-104c on the holonomic motion platform 80 in the coordinate system of the fuselage section 12. More details concerning the operation of an LPS will be provided later with reference to FIG. 15.

The LPS can be used to take discrete measurements at specific times (such as during initialization), while encoders are used to get continuous data. For example, during the initial setup, the LPS is used to determine the position and orientation of the base 84 of the holonomic motion platform 80 with respect to the fuselage section 12. After that, the relative motion data from the encoders are used along with that initial position and orientation data to provide a continuously updated position and orientation of the NDI sensor unit 100. Note that LPS may not be fast enough to capture the measurement data continuously. More importantly, small motions at the NDI sensor unit 100 are captured by the encoder data that would not be possible to accurately detect with measurements taken only at the base 84.

Figure 8:
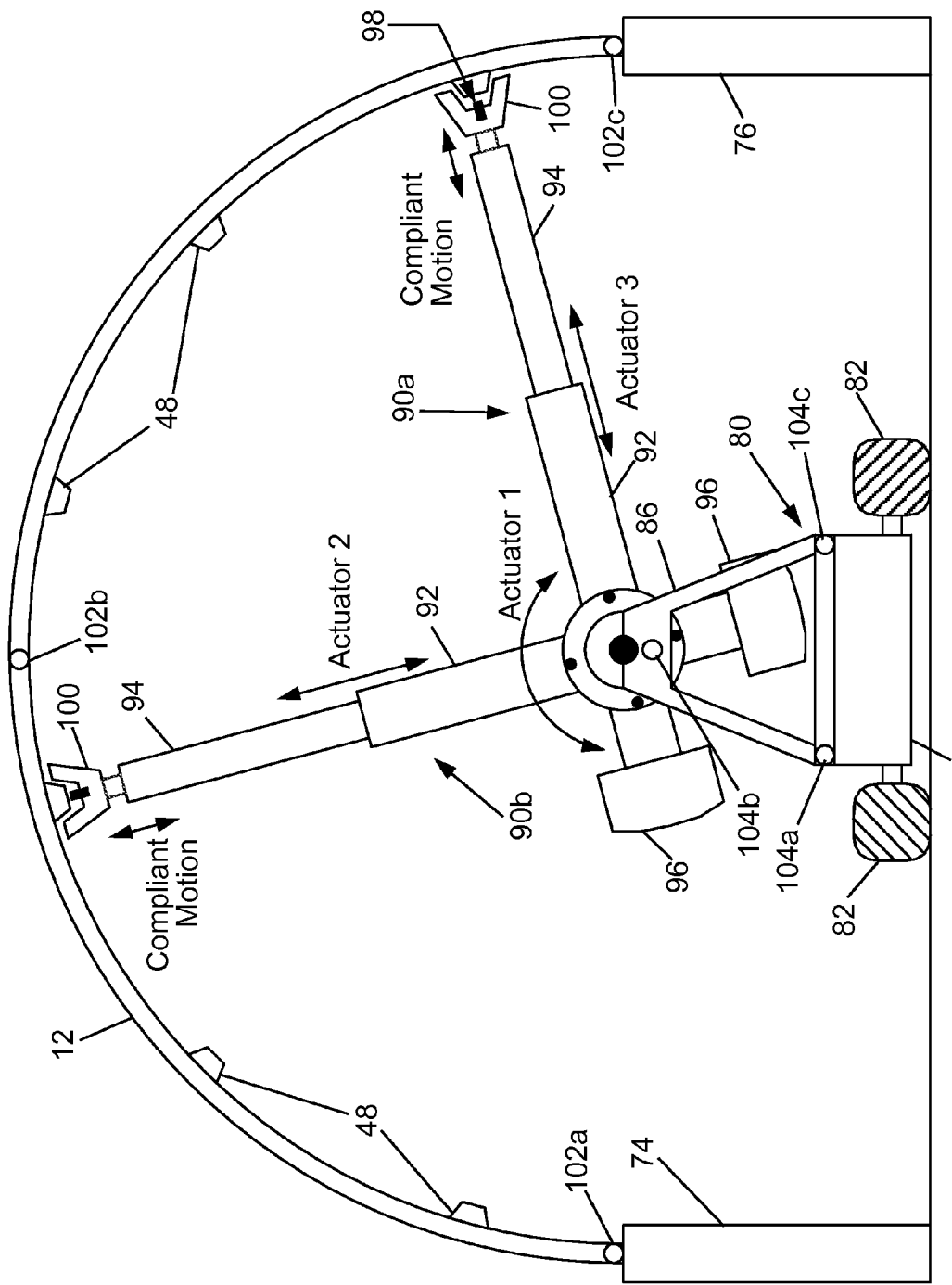
FIG. 8 is a diagram representing an end view of portions of an internal scanning system for scanning stringers of a half-barrel fuselage section, such system having a double arm configuration and comprising a holonomic motion platform with LPS and encoder tracking.

FIG. 8 is a diagram representing an end view of portions of an internal scanning system for scanning stringers 48 of a half-barrel fuselage section 12, such system having a double arm configuration (see extendible arms 90a and 90b) and comprising a holonomic motion platform 80 with LPS tracking. In some embodiments, the outer sleeves 92 of the extendible arms 90a and 90b may have a fixed relationship to each other and may be rotatable together with a single actuator, as indicated by the double-headed arrow labeled "Actuator 1". In other embodiments the two arms may be able to rotate separately using independent actuators. The inner sleeves 94 of the extendible arms 90a and 90b are independently translatable relative to the respective outer sleeves 92, as indicated by the double-headed arrows respectively labeled "Actuator 3" and "Actuator 2" in FIG. 8. The double arm configuration depicted in FIG. 8 enables two NDI sensor units 100 to scan respective stringers 48 concurrently as the holonomic motion platform 80 travels in an X-axis direction.

Figure 9:
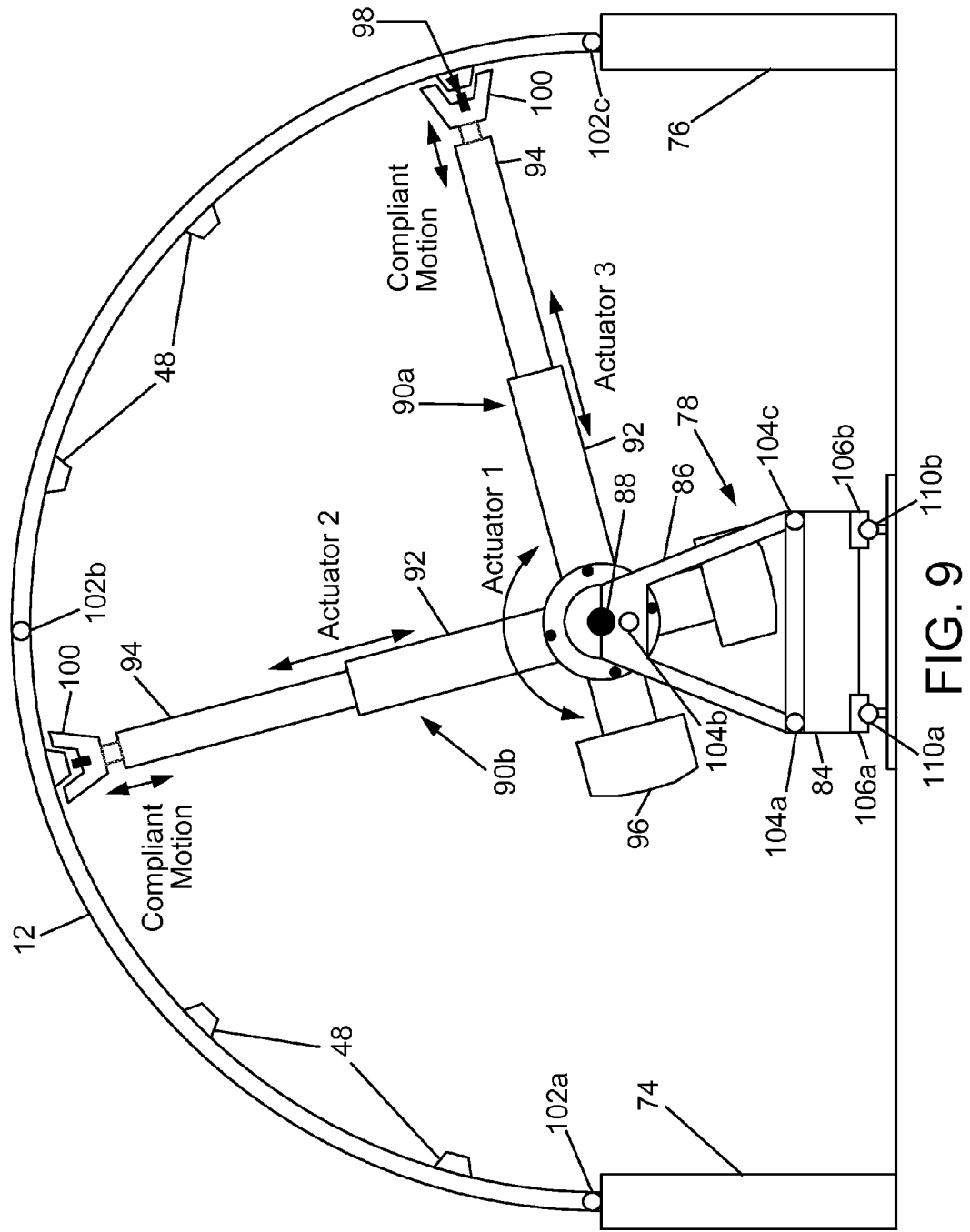
FIG. 9 is a diagram representing an end view of portions of an internal scanning system for scanning stringers of a half-barrel fuselage section, such system having a double arm configuration and comprising a linear motion platform on linear bearings with LPS and encoder tracking.

FIG. 9 shows an end view of portions of an internal scanning system for scanning stringers of a half-barrel fuselage section, such system having the same double arm configuration seen in FIG. 8, but comprising a linear motion platform 78 whose location is tracked using an LPS. The linear motion platform 78 comprises linear bearings 106a and 106b which respectively ride on floor-mounted linear rails 110a and 110b which are parallel to the X-axis direction. As the linear motion platform 78 moves along the X-axis, the NDI sensor units 100 scan respective stringers 48. The instantaneous X-position of each NDI sensor unit can be tracked by respective encoders coupled to respective encoder wheels 98 which roll along respective surfaces of the stringers being inspected. That encoder data is then used to correlate the X-position of each NDI sensor unit to the scan data acquired.

Figure 10:
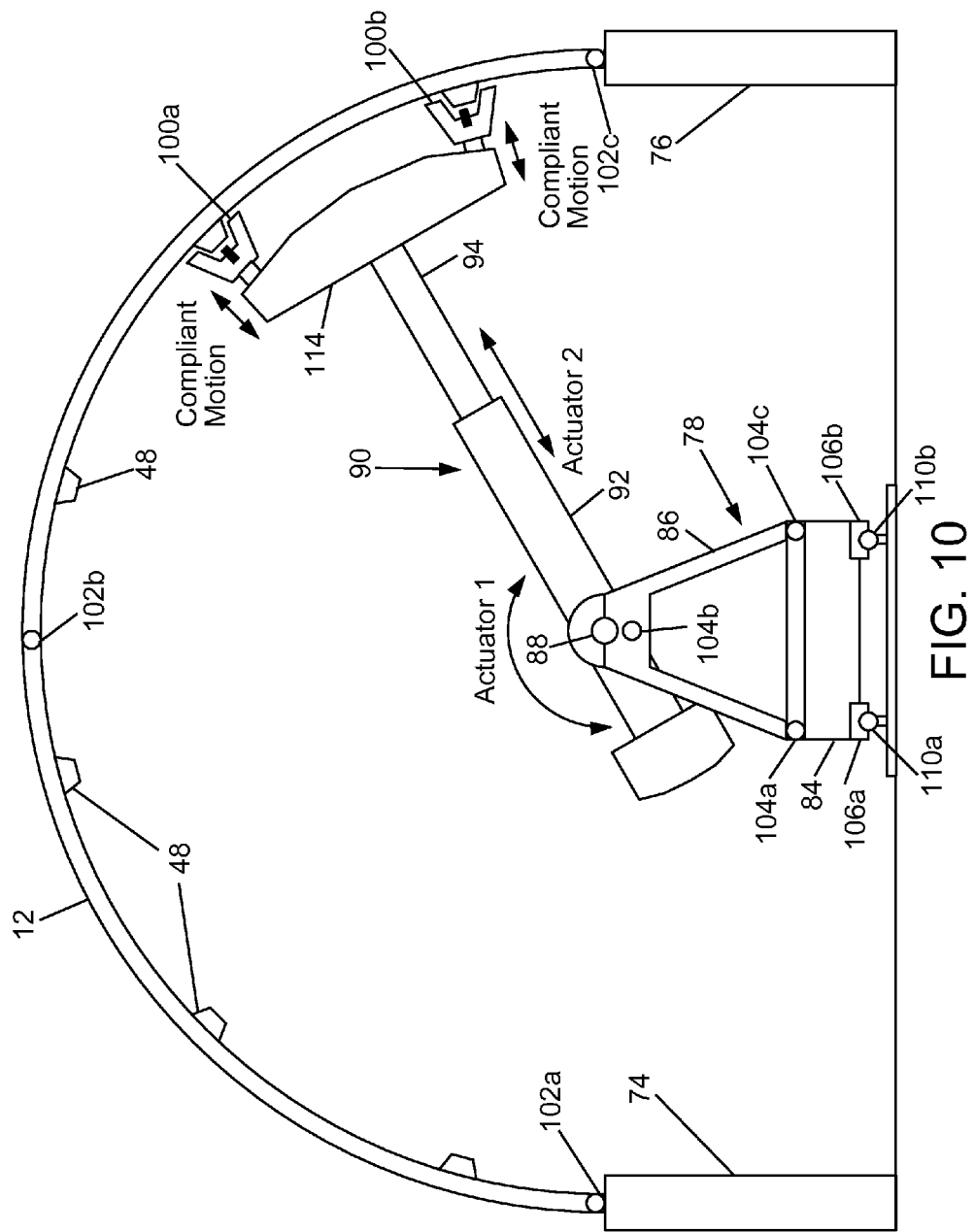
FIG. 10 is a diagram representing an end view of portions of an internal scanning system for scanning stringers of a half-barrel fuselage section, such system having a single arm, double end-effector configuration in accordance with one embodiment and comprising a linear motion platform on linear bearings with LPS and encoder tracking.

FIG. 10 is a diagram representing an end view of portions of an internal scanning system for scanning stringers 48 of a half-barrel fuselage section 12, such system having a single-arm, double-end-effector configuration in accordance with an alternative embodiment. This system comprises a linear motion platform 78 with LPS tracking.

In accordance with the embodiment depicted in FIG. 10, the linear motion platform 78 comprises a base 84, linear bearings 106a and 106b which respectively ride on floor-mounted linear rails 110a and 110b, two motors (not shown, but mounted to the base 84) which respectively actuate translation of the platform along the linear rails 110a and 110b, a frame 86 attached to the base 84, and a pivot joint 88 supported by the frame 86 and connected to the extendible arm 90.

Still referring to FIG. 10, the extendible arm 90 comprises a pivotable outer sleeve 92 connected to the pivot joint 88, an inner sleeve 94 that is translatable inside the outer sleeve 92, a transverse member 114 attached to a distal end of the inner sleeve 94, and a pair of NDI sensor units 100a and 100b coupled to the transverse member 114 by means of respective compliant support structures similar to the compliant support structure 70 previously described in detail with reference to FIG. 4. Such compliant support structures enable each NDI sensor unit to adjust its radial position in response to variations in the size and shape of the corresponding stringer 48 as the NDI sensor unit travels along the length of a stringer. Such compliant motion is indicated by double-headed arrows in FIG. 10.

Figure 11:
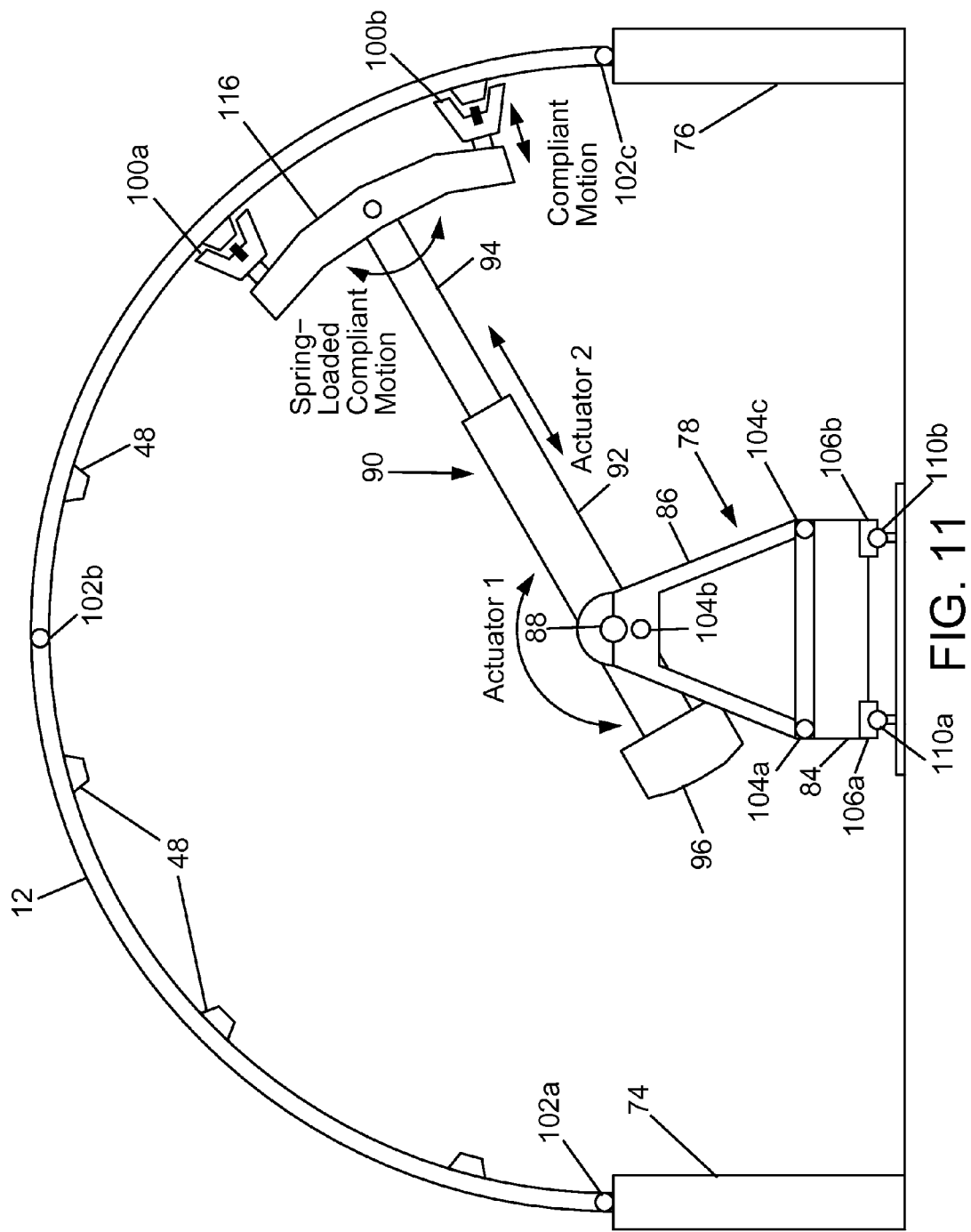
FIG. 11 is a diagram representing an end view of portions of an internal scanning system for scanning stringers of a half-barrel fuselage section, such system having a single arm, double end-effector configuration in accordance with another embodiment and comprising a linear motion platform on linear bearings with LPS and encoder tracking.

FIG. 11 shows an end view of portions of an internal scanning system having a single-arm, double-end-effector configuration in accordance with an alternative embodiment. This embodiment differs from the embodiment shown in FIG. 10 in that, instead of a transverse member affixed to a distal end of the extendible arm 90, a pivotable cross member 116 is pivotably coupled to the distal end of the extendible arm 90. The pivotable coupling preferably includes means for spring-loaded compliant pivoting motion of cross member 116 (which compliant motion is in addition to the compliant motion provided by the compliant support structures which couple the NDI sensor units 100a and 100b to the cross member 116).

Figure 12:
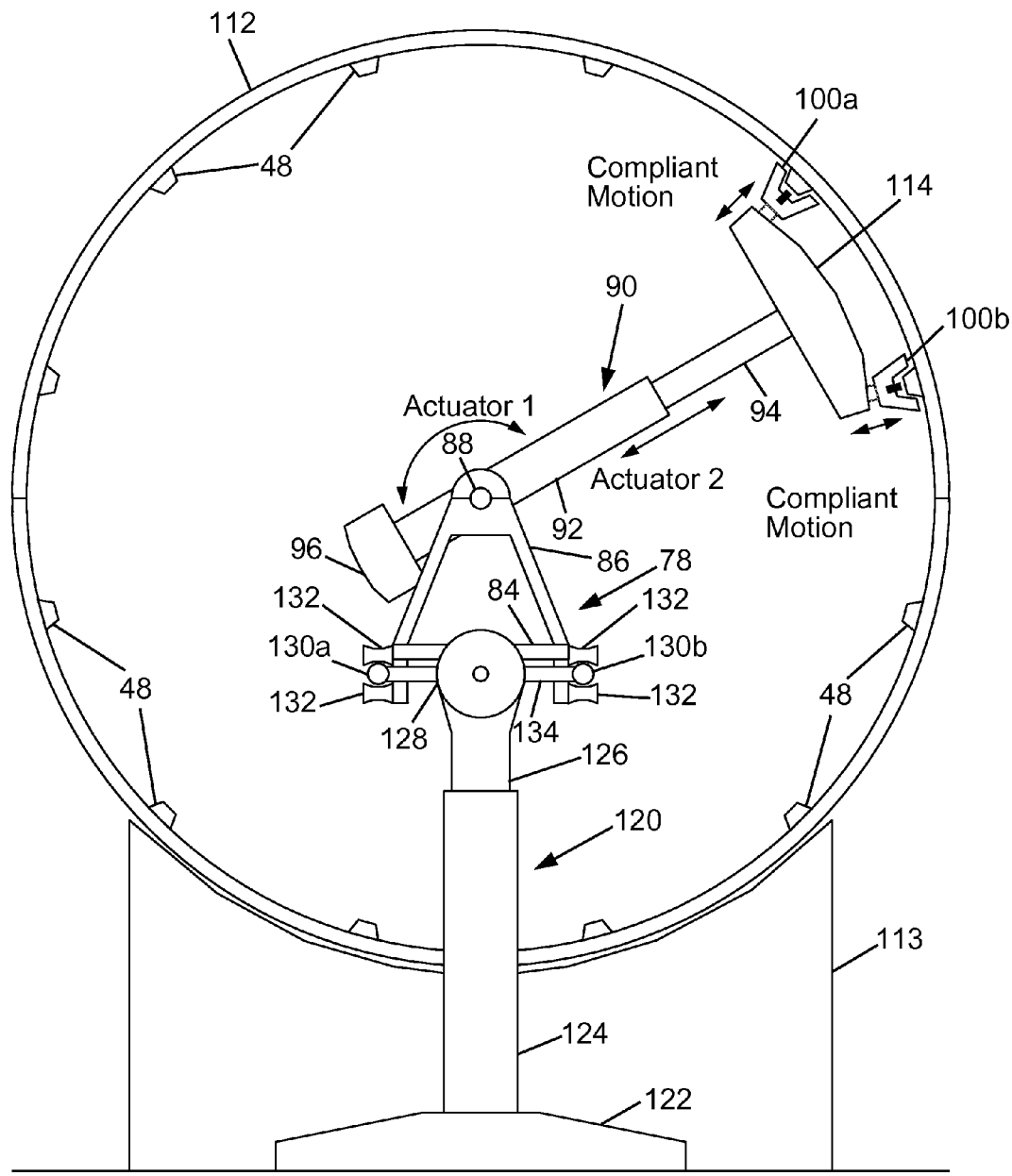
FIGS. 12 and 13 are diagrams representing respective end views of portions of an internal scanning system for scanning stringers of a full-barrel fuselage section, such system having a single arm, double end-effector configuration of the type shown in FIG. 10 and comprising a linear motion platform on rails. The linear motion platform is shown in respective locations for scanning stringers on the upper half (FIG. 12) and lower half (FIG. 13) of a full-barrel fuselage section.
Figure 13:
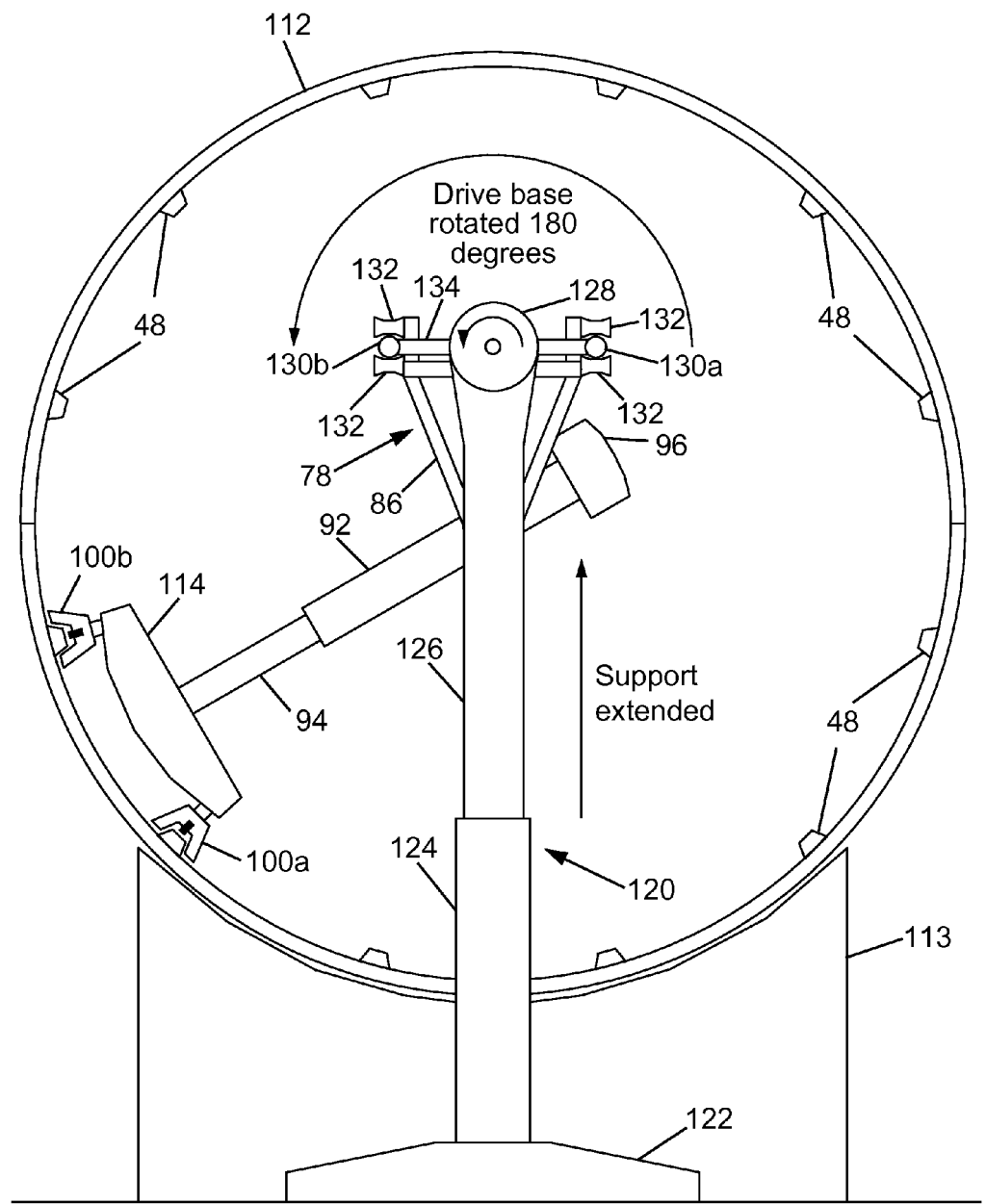

FIGS. 12 and 13 are diagrams representing respective end views of portions of an internal scanning system for scanning stringers of a full-barrel fuselage section 112 supported by a support base 113. This system has a single-arm, double-end-effector configuration of the type shown in FIG. 10 and a linear motion platform 78. The linear motion platform 78 comprises rollers 132 that ride on a pair of linear rails 130a and 130b. In this case the linear rails 130a and 130b are mounted to and supported by a platform lift 120 instead of on the floor.

The linear motion platform 78 is shown in respective locations for scanning stringers 48 on the upper half (FIG. 12) and lower half (FIG. 13) of the full-barrel fuselage section 112. The platform lift 120 comprises a pair of extendible supports which support a bridge beam (see bridge beam 136 in FIG. 14) having a length greater than the length of the fuselage section being inspected. Each extendible support comprises a pedestal 122, a fixed outer sleeve 124 projecting vertically upward from the pedestal 122, an inner sleeve 126 that is translatable inside the outer sleeve 124, and a bearing 128 mounted to a distal end of the inner sleeve 126.

Figure 14:
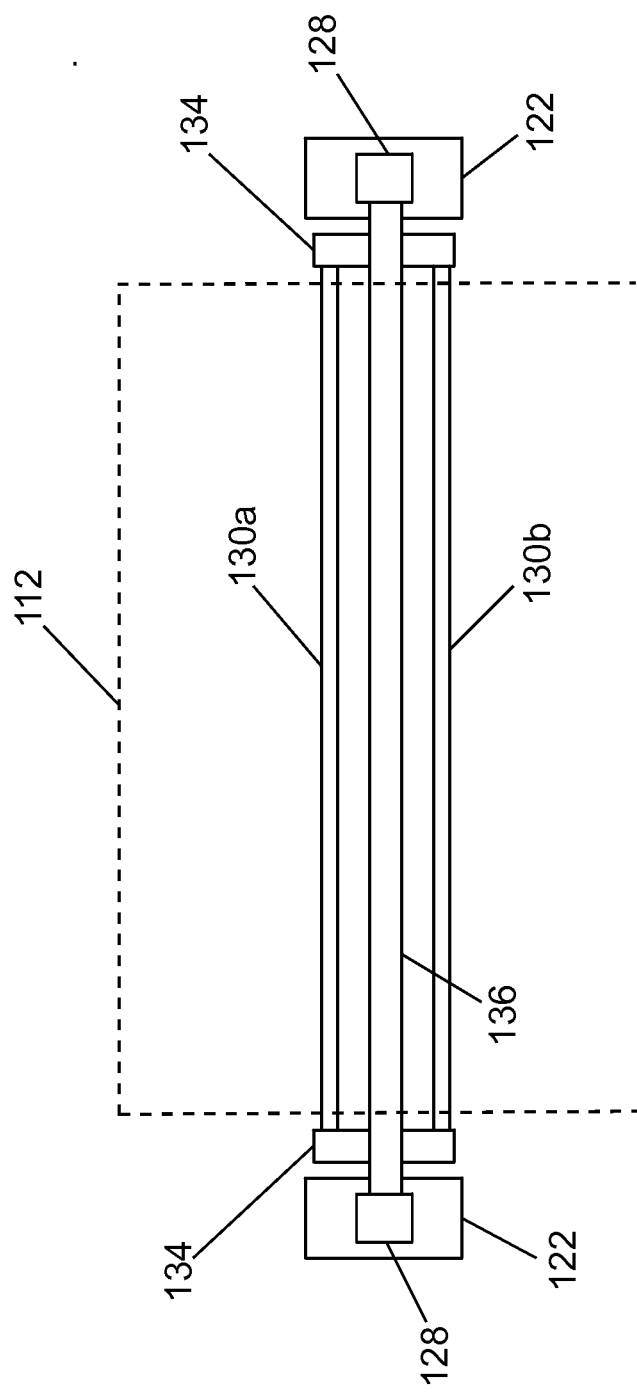
FIG. 14 is a diagram showing a top view of some components of the system depicted in FIGS. 12 and 13. The dashed rectangle indicates the longitudinal and transverse dimensions of a full-barrel fuselage section surrounding a linear motion platform on rails.

FIG. 14 shows a top view of some components of the system depicted in FIGS. 12 and 13. The dashed rectangle indicates the longitudinal and transverse dimensions of a full-barrel fuselage section 112 surrounding linear rails 130a and 130b and a bridge beam 136 of the platform lift. The ends of the linear rails 130a and 130b are respectively connected to respective cross beams 134 which are attached to and project laterally from the bridge beam 136 on both sides thereof. The linear motion platform (not shown in FIG. 14) can travel from one end of linear rails 130a and 130b to the other end.

In order to place a full-barrel fuselage section 112 in the position seen in FIGS. 12 and 13, one end of the platform lift 120 would need to be disassembled while the corresponding end of the bridge beam 136 is supported by other means.

In the configuration shown in FIG. 12, the linear motion platform 78 is upright and the pivot joint 88 is located at a center of the full-barrel fuselage section 112. In this configuration, the stringers 48 attached to the upper half of the full-barrel fuselage section 112 can be scanned.

In the configuration shown in FIG. 13, the supports are extended and the linear motion platform 78 is rotated 180 degrees. The supports are extended by a distance such that the pivot joint 88 is again located at the center of the full-barrel fuselage section 112 when the linear motion platform 78 is upside down. In this configuration, the stringers 48 attached to the lower half of the full-barrel fuselage section 112 can be scanned.

In each of the embodiments depicted in FIGS. 8 through 12, the LPS can be used to take discrete measurements at specific times (such as during initialization), while encoders are used to get continuous data. In accordance with respective alternative embodiments, a motion capture system can be used to track the location of the NDI sensor unit.

Figure 15:
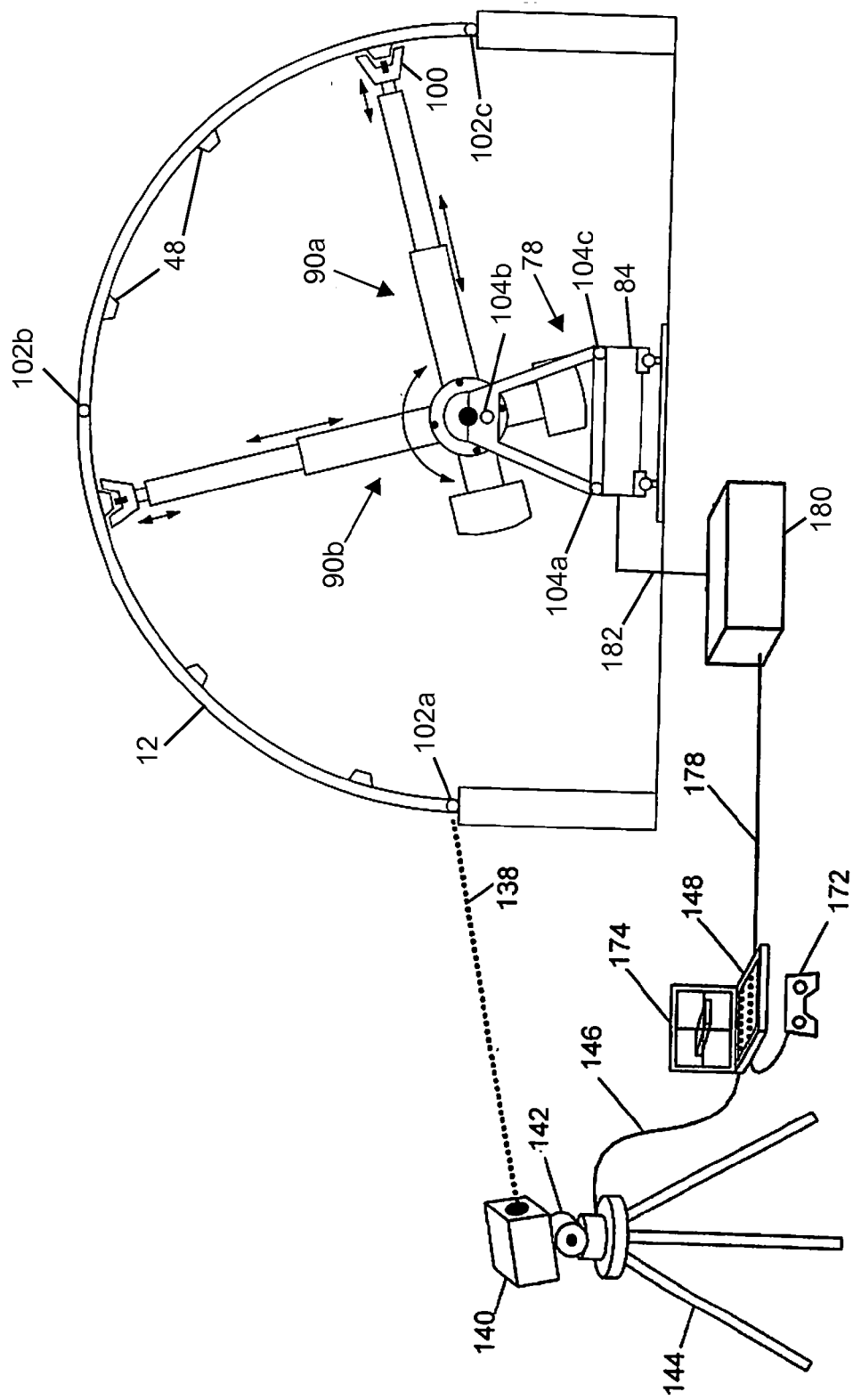
FIG. 15 is a diagram showing a physical setup in which a local positioning system is used to provide a location of a linear motion platform relative to a half-barrel fuselage section.

FIG. 15 shows a physical setup in which an LPS is used to track a location of a linear motion platform 78 relative to a half-barrel fuselage section 12. The LPS comprises a single video camera 140 and a laser range meter (not shown) on a controllable pan-tilt mechanism 142 with angle measurement capability mounted on a tripod 144. The video camera 140 may have automated (remotely controlled) zoom capabilities. The video camera 140 may additionally include an integral crosshair generator to facilitate precise locating of a point within an optical image field display of the video camera. The video camera 140 and pan-tilt mechanism 142 may be operated by an LPS computer 148. The LPS computer 148 communicates with the video camera 140 and the pan-tilt mechanism 142 through a video/control cable 146. Alternatively, the LPS computer 148 may communicate with video camera 140 and pan-tilt mechanism 142 through a wireless communication pathway. The pan and tilt angles of the pan-tilt mechanism 142 and, therefore, the orientation of the video camera 140 can be controlled using the keyboard of the LPS computer 148 or other input device, such as the gamepad interface 172 shown in FIG. 15. The optical image field, with crosshair overlay, as sighted by the video camera 140, can be displayed on the monitor 174 of the LPS computer 148.

The pan-tilt mechanism 142 is controlled to positionally adjust the video camera 140 to selected angles around a vertical, azimuth (pan) axis and a horizontal, elevation (tilt) axis. A direction vector 138, that describes the orientation of the camera 140 relative to the fixed coordinate system of the tripod 144 (or other platform on which the pan-tilt unit is attached), is determined from the pan and tilt angles, as well as the position of the center of a crosshair marker in the optical field when the camera 140 is aimed at a point of interest. This direction vector 138 is depicted in FIG. 15 as a dashed line extending from the lens of the camera 140 and intersecting a calibration point 102a on the fuselage section 12. The other calibration points 102b and 102c on the fuselage section and the calibration points 104a-104c on the linear motion platform 78 will each be targeted in turn and the data thus acquired can be processed by the LPS computer 148 to calculate the position and orientation offset of the linear motion platform 78 relative to the fuselage section 12.

A laser range meter may be incorporated inside the housing of camera 140 or mounted to the outside of camera 140 in such a way that it transmits a laser beam along the direction vector 138. The laser range meter is configured to measure the distance to each calibration point. The laser range meter may have a laser and a unit configured to compute distances based on the laser light detected in response to a laser beam reflected by the each calibration point.

The local positioning system shown in FIG. 15 further comprises three-dimensional localization software which is loaded into the LPS computer 148. For example, the three-dimensional localization software may be of a type that uses multiple non-collinear calibration points 102a-102c on the fuselage section 12 to define the location (position and orientation) of video camera 140 relative to the fuselage section 12. Calibration points 102a-102c can be temporarily attached to the fuselage section 12. Alternatively, features on the fuselage section 12 can be used as calibration points.

The measured distances to the calibration points 102a-102c may be used in coordination with the pan and tilt angles from the pan-tilt mechanism 142 to solve for the camera position and orientation relative to the fuselage section 12. A method for generating an instrument to target calibration transformation matrix (sometimes referred to as the camera pose) is disclosed in U.S. Pat. No. 7,859,655. Using the measured data, the calibration process computes the 4×4 homogeneous transformation matrix that defines the position and orientation of the video camera 140 (and laser range meter) relative to the fuselage section 12.

The LPS seen in FIG. 15 can also be used to determine the position and orientation of the video camera 140 relative to base 84 of the linear motion platform 78. The LPS uses multiple non-collinear calibration points 104a-104c on the base 84 to define the location (position and orientation) of video camera 140 relative to the base 84. Given the location of the fuselage section 12 relative to the video camera 140 and the location of the base 84 relative to the video camera 140, the location of the base 84 relative to the fuselage section 12 can be determined at the start of each work sequence.

During each work sequence, a motion controller 180 can control the base 84 to move in a manner that allows the end effectors 100 to scan respective stiffeners 48 of the fuselage section 12. The LPS computer 148 communicates with the motion controller 180 through a cable 178; the motion controller communicates with actuators (not shown) on the base 84 through a cable 182. The motion controller 180 is preferably a computer programmed with motion control software. The motion controller 180 will be able to control the linear motion of the linear motion platform 78, as well as the location of the end effector 100 of arm 90a (and 90b) based on the starting location (position and orientation) of base 84 relative to fuselage section 12 as calculated by the LPS computer 148.

Using the foregoing methodology, the initial location of a movable scanning platform relative to a stationary fuselage section can be determined. The scanning platform is then moved in the X direction while the first stringer is scanned. During a scan in the X direction, the displacement of the scanning platform relative to its starting position can be tracked using an encoder wheel mounted to an end effector being carried by the scanning platform. Because the starting X position of the end effector relative to the fuselage section is known, the varying X position of the end effector (defined in the coordinate system of the fuselage section) can be tracked. When the end effector reaches the end of the first stringer, the scanning platform can be returned to its starting position, moved to the next stringer location, and then the process can be repeated for the next stringer to be inspected.

The benefits of the internal scanning system disclosed above include scanning at a high rate sufficient to maintain production schedules. The scanner does not have to be repositioned by a human operator for each stringer; instead the mechanism can be programmed to move to the next stringer automatically. Other benefits include simple programming, simple structure, and reduced maintenance costs. The system is modular and can be moved to a new location easily, especially the holonomic motion version.

Figure 16:
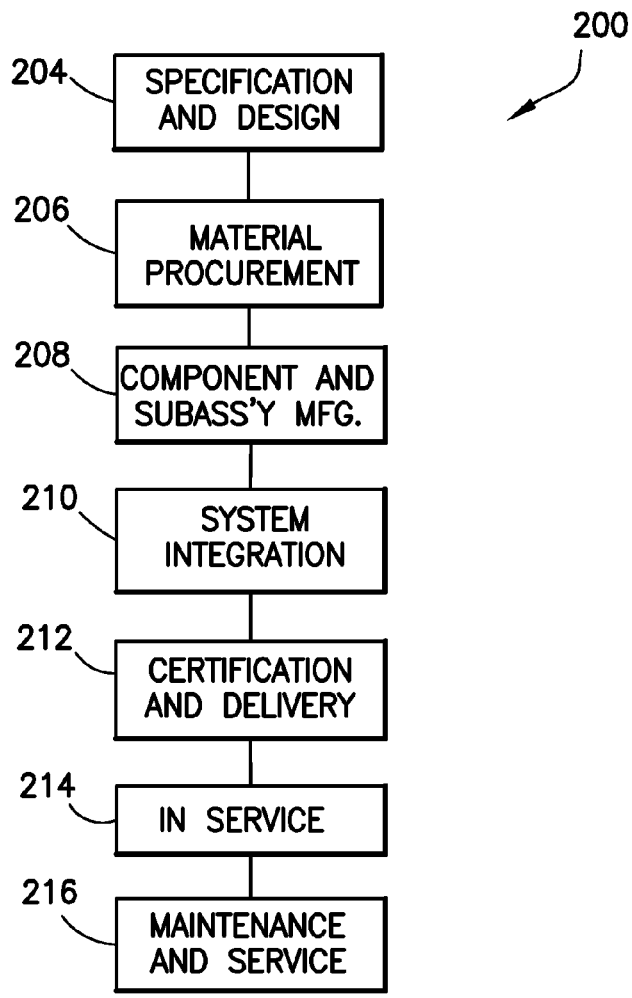
FIG. 16 is a flow diagram of an aircraft production and service methodology.
Figure 17:
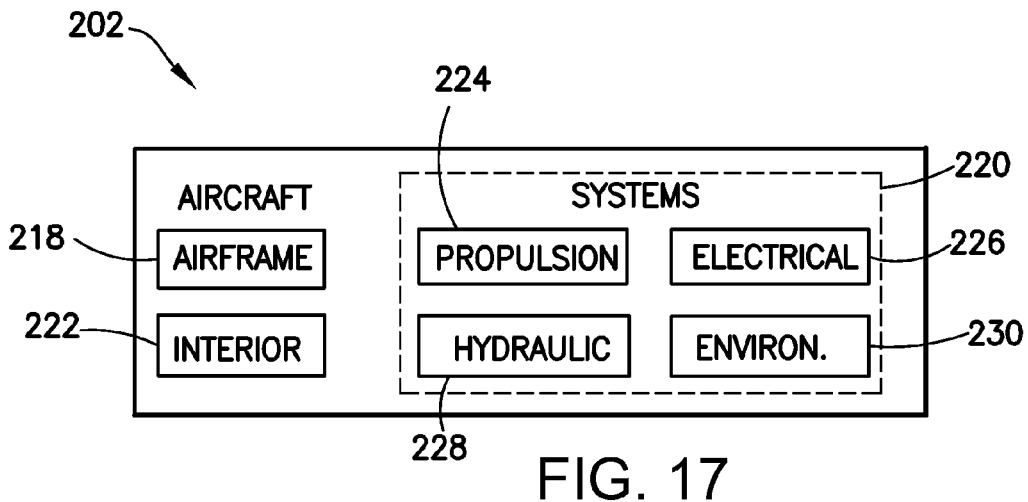
FIG. 17 is a block diagram showing systems of an aircraft.

The systems and methods disclosed above may be employed in an aircraft manufacturing and service method 200 as shown in FIG. 16 for inspecting parts of an aircraft 202 as shown in FIG. 17. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216 (which may also include modification, reconfiguration, refurbishment, and so on).

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 17, the aircraft 202 produced by exemplary method 200 may include an airframe 218 (comprising, e.g., a fuselage, frames, stiffeners, wing boxes, etc.) with a plurality of systems 220 and an interior 222. Examples of high-level systems 220 include one or more of the following: a propulsion system 224, an electrical system 226, a hydraulic system 228, and an environmental control system 230. Any number of other systems may be included.

Although an aerospace example is shown, the principles disclosed herein may be applied to other industries, such as the automotive industry.

Apparatus and methods embodied herein may be employed during any one or more of the stages of the production and service method 200. For example, components or subassemblies fabricated or assembled during production process 208 may be inspected using the inspection system disclosed herein. Also, one or more apparatus embodiments, method embodiments, or a combination thereof may be utilized during the production stages 208 and 210, for example, by substantially expediting assembly of or reducing the cost of an aircraft 202. Similarly, one or more of apparatus embodiments, method embodiments, or a combination thereof may be utilized while the aircraft 202 is in service, for example and without limitation, during maintenance and service 216.

While NDI scanning systems have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit. For example, a computer system may comprise respective processors incorporated in a plurality of devices and a control computer in communication with those processors.

As used in the claims, the term "location" comprises position in a fixed three-dimensional coordinate system and orientation relative to that coordinate system.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude two or more steps or portions thereof being performed concurrently or to exclude any portions of two or more steps being performed alternatingly.

The invention claimed is:

1. A method for scanning a workpiece having a curved section that extends longitudinally and circumferentially, the method comprising:
    (a) moving a curved track along first and second linear tracks to a first longitudinal position, the curved track in the first longitudinal position being disposed radially outward from the curved section of the workpiece;
    (b) adjusting a position of an NDI sensor unit relative to a carriage to which the NDI sensor unit is adjustably coupled by an extendible arm, the carriage in turn being movable along the curved track;
    (c) moving the carriage along the curved track while the curved track is stationary at the first longitudinal position;
    (d) during step (c), activating the NDI sensor unit to inspect a first strip-shaped area of the curved section of the workpiece;
    (e) processing signals output from the NDI sensor unit to derive a first strip of scan data characterizing a structural state of the first strip-shaped area of the curved section of the workpiece;
    (f) during step (c), acquiring location data representing locations of the NDI sensor unit relative to the workpiece; and
    (g) mapping the first strip of scan data to a three-dimensional model of the workpiece based on the location data acquired in step (f).

2. The method as recited in claim 1, further comprising displaying features overlaid on a representation of a portion of the three-dimensional model of the workpiece based on the results of steps (e) and (g).

3. The method as recited in claim 1, wherein the workpiece has a shape of a full barrel, further comprising rotating the workpiece about a longitudinal axis and then repeating steps (a) through (g).

4. The method as recited in claim 1, further comprising the following steps:
    (h) subsequent to step (c), moving the curved track along the first and second linear tracks from the first longitudinal position to a second longitudinal position, the curved track in the second longitudinal position being disposed radially outward from the curved section of the workpiece;
    (i) moving the carriage along the curved track while the curved track is stationary at the second longitudinal position;
    (j) during step (i), activating the NDI sensor unit to inspect a second strip-shaped area of the curved section of the workpiece;
    (k) processing signals output from the NDI sensor unit to derive a second strip of scan data characterizing a structural state of the second strip-shaped area of the curved section of the workpiece;
    (l) during step (i), acquiring location data representing locations of the NDI sensor unit relative to the workpiece using the location tracking system; and
    (m) mapping the second strip of scan data to the three-dimensional model of the workpiece based on the location data acquired in step (l).

5. The method as recited in claim 4, wherein step (h) comprises generating pulses representing incremental longitudinal movements of the curved track along a stationary linear rail and step (i) comprises generating pulses representing incremental circumferential movements of the NDI sensor unit along the curved track.

6. The method as recited in claim 5, further comprising:
    converting the location data representing the locations of the NDI sensor unit during step (c) into simulated encoder pulses suitable for processing by non-destructive inspection scan software; and
    correlating the simulated encoder pulses with the first strip of scan data.

7. The method as recited in claim 4, wherein step (h) comprises the following steps performed during steps (c) and (e): emitting light directed toward retro-reflective targets affixed to the NDI sensor unit; and capturing returned light reflected by said retro-reflective targets, and step (i) comprises computing location data representing the locations of the NDI sensor unit relative to the workpiece based on the captured returned light.

8. The method as recited in claim 1, wherein the workpiece is a fuselage section.

9. The method as recited in claim 8, wherein the fuselage section is made of composite material.

10. A system for external scanning of a workpiece having a curved outer mold line, the system comprising:
   first and second linear tracks which are mutually parallel;
   a curved track disposed in a plane generally transverse to said first and second linear tracks, said curved track being coupled to and translatable relative to said first and second linear tracks;
   a carriage coupled to and movable along said curved track;
   an extendible arm having a proximal end coupled to said carriage;
   an NDI sensor unit coupled to a distal end of said extendible arm;
   a location tracking system capable of tracking the location of said NDI sensor unit relative to said workpiece; and
   a data processing system capable of receiving scan data from said NDI sensor unit and location tracking data from said location tracking system and then correlating the scan data with the location tracking data.

11. The system as recited in claim 10, wherein said location tracking system comprises a plurality of cameras, a first plurality of retro-reflective markers attached to the workpiece and arranged in a known pattern; a second plurality of retro-reflective markers attached to the NDI sensor unit and arranged in a known pattern, and a motion capture processor.

12. The system as recited in claim 10, wherein said extendible arm comprises a first member coupled to said carriage and a second member which is translatable relative to said first member, and said location tracking system comprises:
   a first encoder device that outputs signals representing incremental movements of said curved track along said linear tracks;
   a second encoder device that outputs signals representing incremental movements of said carriage along said curved track;
   a third encoder device that outputs signals representing a distance that said second member of said extendible arm has traveled relative to said first member; and
   a computer system programmed to be capable of converting the output signals from said first through third encoder devices into location data representing locations of said NDI sensor unit.

13. The system as recited in claim 10, further comprising a display system capable of displaying the scan data on a three-dimensional representation of the workpiece based on results of the correlating process performed by said data processing system.

14. A system for scanning a workpiece having a curved section that extends longitudinally and circumferentially, the system comprising:
   a pair of linear tracks parallel to a longitudinal direction;
   an arch frame that extends circumferentially and is arranged to travel along said linear tracks;
   a first actuator which, when activated, causes said arch frame to travel along said linear tracks;
   a curved track supported by said arch frame;
   a carriage arranged to travel along said curved track;
   a second actuator which, when activated, causes said carriage to travel along said curved track;
   an extendible arm comprising a first member mounted to said carriage and a second member which is arranged to translate relative to said first member;
   a third actuator which, when activated, causes said second member to translate relative to said first member; and
   an NDI sensor unit mounted to said second member and operable to acquire scan data during its motion.

15. The system as recited in claim 14, further comprising:
   a first encoder device that outputs signals representing incremental movements of said arch frame along said linear tracks;
   a second encoder device that outputs signals representing incremental movements of said carriage along said curved track;
   a third encoder device that outputs signals representing a distance that said second member of said extendible arm has traveled relative to said first member; and
   a computer system programmed to be capable of performing the following operations:
   (a) tracking the location of said NDI sensor unit to acquire location data representing locations of said NDI sensor unit based on signals outputted by said first, second and third encoder devices;
   (b) controlling said first, second and third actuators to cause said NDI sensor unit to travel along said curved track from a first circumferential position to a second circumferential position while said NDI sensor unit is adjacent to an outer mold line of the workpiece and said curved track is stationary;
   (c) while said NDI sensor unit is traveling along said curved track from the first circumferential position to the second circumferential position and said curved track is stationary, controlling said NDI sensor unit to interrogate the workpiece and acquire a strip of scan data; and
   (d) mapping the strip of scan data to a three-dimensional model of the workpiece based on location data acquired as said NDI sensor unit travels along said curved track from the first circumferential position to the second circumferential position.

16. The system as recited in claim 15, further comprising a display monitor, wherein said computer system is further programmed to control said display monitor to display the strip of scan data overlaid on an image of a three-dimensional representation of the workpiece.

17. The system as recited in claim 16, wherein said computer system comprises:
   a data acquisition device connected to receive signals outputted by said second and third encoder devices and programmed to convert those signals into simulated encoder pulses; and
   an inspection scanning subsystem connected to receive simulated encoder pulses from said data acquisition device and scan data from said NDI sensor unit, and programmed to decode received simulated encoder pulses into position data and then associate that position data with the scan data for display, wherein the position data represents coordinates of said NDI sensor unit with respect to the coordinate system of the workpiece.

18. The system as recited in claim 14, further comprising:
   a first plurality of retro-reflective markers attached to the workpiece;
   a second plurality of retro-reflective markers attached to said arch frame;
   a third plurality of retro-reflective markers attached to said extendible arm;

a plurality of cameras having said retro-reflective markers within respective fields of view;

a motion capture subsystem programmed to convert images from said cameras into calibration data representing a position and an orientation of the workpiece with respect to a motion capture coordinate system and first location data representing positions and orientations of said NDI sensor unit with respect to the motion capture coordinate system during movement of said NDI sensor unit; and a motion tracking subsystem connected to receive said first location data from said motion capture subsystem and programmed to output second location data which is a function of the first location data received from said motion capture subsystem, said second location data representing positions and orientations of said NDI sensor unit with respect to a coordinate system of the workpiece.

19. The system as recited in claim 18, further comprising:
a data acquisition device connected to receive said second location data from said motion tracking subsystem and programmed to convert portions of said second location data received from said motion tracking subsystem into simulated encoder pulses; and
an inspection scanning subsystem connected to receive simulated encoder pulses from said data acquisition device and scan data from said NDI sensor unit, and programmed to decode received simulated encoder pulses into position data and then associate that position data with the scan data for display, wherein the position data represents coordinates of said NDI sensor unit with respect to the coordinate system of the workpiece.

20. The system as recited in claim 19, further comprising a display monitor and a display computer programmed to control said display monitor to display the scan data overlaid on an image of a three-dimensional representation of the workpiece.

21. A system for scanning a workpiece having a curved section that extends longitudinally and circumferentially, the system comprising:
a pair of linear tracks parallel to a longitudinal direction;
a curved track that extends circumferentially and is arranged to travel along said linear tracks;
a first actuator which, when activated, causes said curved track to travel along said linear tracks;
a carriage arranged to travel along said curved track;
a second actuator which, when activated, causes said carriage to travel along said curved track;
an extendible arm comprising a first member mounted to said carriage and a second member which is arranged to translate relative to said first member;
a third actuator which, when activated, causes said second member to translate relative to said first member; and
an NDI sensor unit mounted to said second member and operable to acquire scan data during its motion.

22. The system as recited in claim 21, further comprising:
a first encoder device that outputs signals representing incremental movements of said curved track along said linear tracks;
a second encoder device that outputs signals representing incremental movements of said carriage along said curved track;
a third encoder device that outputs signals representing a distance that said second member of said extendible arm has traveled relative to said first member; and
a computer system programmed to be capable of performing the following operations:
(a) tracking the location of said NDI sensor unit to acquire location data representing locations of said NDI sensor unit based on signals outputted by said first, second and third encoder devices;
(b) controlling said first, second and third actuators to cause said NDI sensor unit to travel along said curved track from a first circumferential position to a second circumferential position while said NDI sensor unit is adjacent to an outer mold line of the workpiece and said curved track is stationary;
(c) while said NDI sensor unit is traveling along said curved track from the first circumferential position to the second circumferential position and said curved track is stationary, controlling said NDI sensor unit to interrogate the workpiece and acquire a strip of scan data; and
(d) mapping the strip of scan data to a three-dimensional model of the workpiece based on location data acquired as said NDI sensor unit travels along said curved track from the first circumferential position to the second circumferential position.

23. The system as recited in claim 22, further comprising a display monitor, wherein said computer system is further programmed to control said display monitor to display the strip of scan data overlaid on an image of a three-dimensional representation of the workpiece.

* * * * *